(12) United States Patent
Lu et al.

(10) Patent No.: US 6,225,302 B1
(45) Date of Patent: May 1, 2001

(54) AMIDINO PROTEASE INHIBITORS

(75) Inventors: Tianbao Lu, Exton; Bruce E. Tomczuk, Collegeville; Carl R. Illig, Phoenixville, all of PA (US); Richard M. Soll, Lawrenceville, NJ (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 0 days.

(21) Appl. No.: 09/631,107

(22) Filed: Aug. 1, 2000

Related U.S. Application Data

(62) Division of application No. 09/270,734, filed on Mar. 16, 1999, now Pat. No. 6,133,315, which is a division of application No. 08/782,894, filed on Dec. 27, 1996, now Pat. No. 6,034,127.

(60) Provisional application No. 60/009,431, filed on Dec. 29, 1995.

(51) Int. Cl.$^7$ .................. A61K 31/445; C07D 211/62
(52) U.S. Cl. .................. 514/183; 514/217.12; 514/331; 540/483; 540/609; 546/231
(58) Field of Search .................. 540/483, 609; 546/231; 514/181, 217.12, 331

(56) References Cited

U.S. PATENT DOCUMENTS

| | | | |
|---|---|---|---|
| 3,577,432 | 5/1971 | Helsley | 260/326.3 |
| 4,316,889 | 2/1982 | Bajusz et al. | 424/177 |
| 4,433,152 | 2/1984 | Muramatsu et al. | 546/193 |
| 5,260,307 | 11/1993 | Ackermann et al. | 514/323 |
| 5,466,811 | 11/1995 | Alexander | 546/283 |

FOREIGN PATENT DOCUMENTS

| | | |
|---|---|---|
| 0 372 486 | 6/1990 | (EP) . |
| 0 559 046 | 9/1993 | (EP) . |
| 50-140474 | 11/1975 | (JP) . |
| 51-75042 | 6/1976 | (JP) . |
| 58-194861 | 11/1983 | (JP) . |
| WO 93/16036 | 8/1993 | (WO) . |
| WO 94/20467 | 9/1994 | (WO) . |
| WO 96/06832 | 3/1996 | (WO) . |
| WO 96/06849 | 3/1996 | (WO) . |
| WO 97/11693 | 4/1997 | (WO) . |

OTHER PUBLICATIONS

Baker, B.R. and E.H. Erickson, "Irreversible Enzyme Inhibitors. CLII. Proteolytic Enzymes. X. Inhibition of Guinea Pig Complement by Substituted Benzamidines," *J. Med. Chem.* 12:408–414 (1969).

Benkert, B. et al., "Relations between structure and the noradrenaline depleting effects of guanidine and amidine derivatives," *Chem. Abst.* 83:188217s (1975).

Brzozowski, Z., "Derivatives of 2–mercaptobenzenesulfonamide. I. Synthesis of some S–0 and N–substituted derivatives of 4–chloro–2–mercapto–5–methylbenzenesulfonamide," *Acta Pol. Pharm.* 44(6):486–490 (1987).

Coats, E.A., "Comparative Inhibition of Thrombin, Plasmin, Trypsin, and Complement by Benzamidines Using Substituent Constants and Regression Analysis," *J. Med. Chem.* 16:1102–1106 (1973).

Geratz, J.D. et al., "New Aromatic Diamidines with Central α–Oxyalkane or α,ω–Dioxyalkane Chains. Structure–Activity Relationships for the Inhibition of Trypsin, Pancreatic Kallikrein, and Thrombin and for the Inhibition of the Overall Coagulation Process," *J. Med. Chem.* 18:477–481

Jameson, G. W. and D. T. Elmore, "Affinity Chromatography of Bovine Trypsin. A Rapid Seraration of Bovine α–and β–Trypsin," *Biochem. J.* 41:555–565 (1974).

Lespagnol, A. et al., "Investigation of the series of diuretic sulfonamide derivatives," *Chem. Abstr.* 63:525 (1965).

Miyamoto, S. and M. Kojima, "N$^4$–(ω–Guanidinoalkanoyl)sulfanilamides," *Chem. Abstr.* 85:159726t (1976), English abstract of JP 51–75042.

Mori, S. et al., "Inhibition of growth of HeLa cells by new synthetic protease inhibitors," *Chem. Abs.* 101:29–30, Abstract No. 65645n (1984).

Nippon Chemifar Co., Ltd., "Piperidine derivatives," *Chem. Abstr.* 101:38355m (1984), English abstract of JP 58–194861.

Protiva, M. et al., "Hypotensive 1–benzyl–4–guanylpiperazines," *Chem. Abstr.* 82:140187j (1975).

Ryznerski, Z. et al., "Synthesis and Pharmacological Properties of Phenoxyethylpiperazine Derivatives," *Pol. J. Pharmacol. Pharm.* 41:191–199 (1989).

Saulnier, M. G. et al., "An Efficient Method for the Synthesis of Guanidino Prodrugs," *Bioorgan. Med. Chem. Letts.* 4(16):1985–1990 (1994).

Somorin, O. and L. Ameghashitsi, "Synthesis of New Arginine Derivatives as Substrates of Trypsin," *Bull. Chem. Soc. Jpn.* 59:1593–1595 (1986).

Takahashi, T. and H. Sugimoto, "Quinazoline compounds," *Chem. Abstr.* 85:46769 (1976), English abstract of JP 50–140474.

Anderskewitz, R. et al., "Novel Amidine derivatives, their preparation, and their use as medicaments with LTB4–antagonistic effect," *Chemical Abstracts, STN International*, Accession No. 120:77038 (1993).

Primary Examiner—Richard L. Raymond
(74) *Attorney, Agent, or Firm*—Sterne, Kessler, Goldstein & Fox P.L.L.C.

(57) ABSTRACT

Amidino and benzamidino compounds, including compounds of the formula:

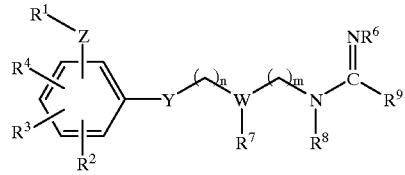

wherein $R^1$–$R^4$, $R^6$–$R^9$, Y, Z, n and m are set forth in the specification, as well as hydrates, solvates or pharmaceutically acceptable salts thereof, that inhibit a number of proteolytic enzymes are described. Also described are methods for preparing the compounds of Formula I.

26 Claims, No Drawings

AMIDINO PROTEASE INHIBITORS

This is a division of U.S. patent application Ser. No. 09/270,734, filed Mar. 16, 1999, now U.S. Pat. No. 6,133,315 which is a division of U.S. application Ser. No. 08/782,894, filed on Dec. 27, 1996, now U.S. Pat. No. 6,034,127, which claims the benefit, under 35 U.S.C. § 119(e), of the earlier filing date of U.S. provisional application, Appl. No. 60/009,431, filed on Dec. 29, 1995. The entirety of each of these applications is incorporated by reference herein.

BACKGROUND OF THE INVENTION

1. Field of the Invention

The present invention relates to novel compounds that function as enzyme inhibitors, and particularly to a new class of non-peptidic inhibitors of proteolytic enzymes.

2. Related Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs*, Sandler, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons (Tapparelli et al., *Trends in Pharmacological Sciences* 14:366–376 (1993); Lefkovits and Topol, *Circulation* 90(3): 1522–1536 (1994); Harker, *Blood Coagulation and Fibrinolysis* 5 (*Suppl* 1):S47–S58 (1994)). Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4):270–277 (1994)), and auto-amplifies its own production through a feedback mechanism. Thus, inhibitors of thrombin function have therapeutic potential in a host of cardiovascular and non-cardiovascular diseases, including: myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; and Down's syndrome.

Factor Xa is another serine protease in the coagulation pathway. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (*Suppl* 1):S47–S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522–1536 (1994); Harker, *Blood Coagulation and Fibrinolysis* 5 (*Suppl* 1):S47–S58 (1994)).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

SUMMARY OF THE INVENTION

The present invention is directed to novel compounds having one of Formulae I–III (below). Also provided are processes for preparing compounds of Formulae I–III. The novel compounds of the present invention are potent inhibitors of proteases, especially trypsin-like serine proteases, such as chymotrypsin, trypsin, thrombin, plasmin and factor Xa Certain of the compounds exhibit antithrombotic activity via direct inhibition of thrombin, or are intermediates useful for forming compounds having antithrombotic activity. Other compounds are inhibitors of trypsin and/or chymotrypsin, and are therefore useful in treating pancreatitis. Also provided are methods of inhibiting or treating aberrant proteolysis in a mammal and methods of treating thrombosis, ischemia, stroke, restenosis or inflammation in a mammal by administering an effective amount of a compound of Formulae I–III. Further provided are pharmaceutical compositions comprising a compound of Formulae I–III and one or more pharmaceutically acceptable carriers or diluents.

DETAILED DESCRIPTION OF THE PREFERRED EMBODIMENTS

Compounds of the present invention include compounds having one of Formulae I–III:

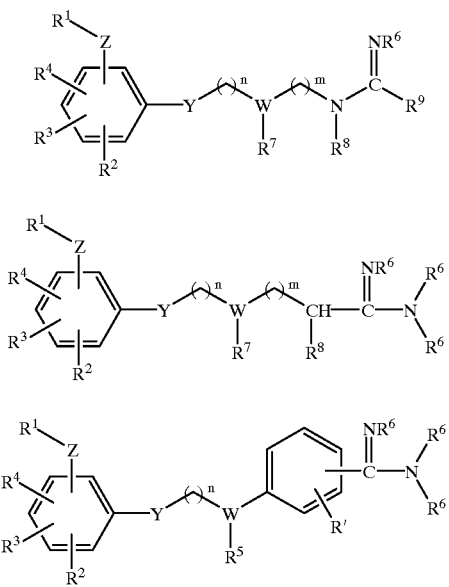

or solvates, hydrates or pharmaceutically acceptable salts thereof; wherein:

Z is one of —NR$^{10}$SO$_2$—, —SO$_2$NR$^{10}$—, —NR$^{10}$C(R$^y$R$^z$)—, —C(R$^y$R$^z$)NR$^{10}$—, —OSO$_2$—, —SO$_2$O—, —OC(R$^y$R$^z$)—, —C(R$^y$R$^z$)O—, —NR$^{10}$CO— or —CONR$^{10}$—;

R$^y$ and R$^z$ are each independently one of hydrogen, alkyl, cycloalkyl, aryl, aralkyl, hydroxyalkyl, carboxyalkyl, aminoalkyl, monoalkylaminoalkyl, dialkylaminoalkyl or carboxy;

R$^1$ is one of alkyl, cycloalkyl, alkenyl, alkynyl, aryl, aralkyl or heteroaryl, any of which may be optionally substituted;

R$^2$, R$^3$ and R$^4$ are each independently one of hydrogen, alkyl, cycloalkyl, alkenyl, alkynyl, aryl, aralkyl, heteroaryl, trifluoromethyl, halogen, hydroxyalkyl, cyano, nitro, carboxamide, —CO$_2$R$^x$, —CH$_2$OR$^x$ or —OR$^x$, or when present on adjacent carbon atoms, R$^2$ and R$^3$ may also be taken together to form one of —CH=CH—CH=CH— or —(CH$_2$)$_q$—, where q is from 2 to 6, and R$^4$ is defined as above;

R$^x$, in each instance, is independently one of hydrogen, alkyl or cycloalkyl wherein said alkyl or cycloalkyl groups may optionally have one or more unsaturations;

Y is one of —O—, —NR$^{10}$—, —S—, —CHR$^{10}$— or a covalent bond;

W is N or CR$^{10}$;

R$^5$ is one of hydrogen, alkyl, aralkyl, aryl, hydroxyalkyl or carboxyalkyl;

R$^6$, in each instance, is independently one of hydrogen, alkyl, hydroxy, alkoxy, aryloxy, aralkoxy, alkoxycarbonyloxy, cyano or —CO$_2$R$^w$, where R$^w$ is alkyl or cycloalkyl;

R$^7$ and R$^8$ are each independently one of hydrogen, alkyl, aralkyl, aryl, hydroxyalkyl or carboxyalkyl, or R$^7$ and R$^8$ are taken together to form —(CH$_2$)$_y$—, where y is zero, 1 or 2, with the proviso that when W is N, y cannot be zero or 1;

R$^9$ is one of hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl;

R$^{10}$, in each instance, is independently one of hydrogen, alkyl, aralkyl, aryl, hydroxyalkyl, aminoalkyl, monoalkylamino(C$_{2-10}$)alkyl, dialkylamino (C$_{2-10}$) alkyl or carboxyalkyl;

R' is one of hydrogen, alkyl, cycloalkyl, aryl, aralkyl, heteroaryl, trifluoromethyl, halogen, hydroxyalkyl, cyano, nitro, carboxamide, carboxy, alkoxycarbonyl or alkoxyalkyl;

n is from zero to 8, with the proviso that when W is N and Y is other than —CHR$^{10}$—, then n is from 2 to 8; and m is from 1 to 4, provided that when W is N, then m is not 1.

A preferred group of compounds falling within the scope of the present invention include compounds of Formulae I–III wherein:

Z is one of —SO$_2$O—, —SO$_2$NR$^{10}$—, —C(R$^y$R$^z$)O— or —OC(R$^y$R$^z$)—, where R$^y$ and R$^z$ are each hydrogen;

R$^1$ is one of C$_{6-10}$ aryl, pyridinyl, quinizolinyl, quinolinyl or tetrahydroquinolinyl, any of which is optionally substituted by one or two of hydroxy, nitro, trifluoromethyl, halogen, C$_{1-6}$ alkyl, C$_{1-6}$ alkoxy, C$_{1-6}$ aminoalkyl, C$_{1-6}$ aminoalkoxy, amino, mono(C$_{1-4}$)alkylamino, di(C$_{1-4}$)alkylamino, C$_{2-6}$ alkoxycarbonylamino, C$_{2-6}$ alkoxycarbonyl, carboxy, C$_{1-6}$ hydroxyalkyl, C$_{2-6}$ hydroxyalkoxy, C$_{2-10}$ mono (carboxyalkyl)amino, di(C$_{2-10}$ carboxyalkyl)amino, C$_{6-14}$ ar(C$_{1-6}$) alkoxycarbonyl, C$_{2-6}$ alkynylcarbonyl, C$_{1-6}$ alkylsulfonyl, C$_{2-6}$ alkenylsulfonyl, C$_{2-6}$ alkynylsulfonyl, C$_{1-6}$ alkylsulfinyl, C$_{1-6}$ alkylsulfonamido, amidino, guanidino, C$_{1-6}$ alkyliminoamino, formyliminoamino, C$_{2-6}$ carboxyalkoxy, C$_{2-6}$ carboxyalkyl, carboxyalkylamino, cyano, trifluoromethoxy, and perfluoroethoxy;

R$^2$, R$^3$ and R$^4$ are independently one of hydrogen, C$_{1-6}$ alkyl, C$_{3-8}$ cycloalkyl, phenyl, benzyl, trifluoromethyl, halogen, hydroxy(C$_{1-8}$)alkyl, cyano, nitro, carboxamide, carboxy, C$_{1-4}$ alkoxycarbonyl, C$_{1-4}$ alkoxymethyl or C$_{1-4}$ alkoxy; or alternatively, R$^2$ and R$^3$, when present on adjacent carbon atoms, may also be taken together to form one of —CH=CH—CH=CH— or —(CH$_2$)$_q$—, where q is from 2 to 6, and R$^4$ is as defined above;

Y is one of —O—, —S—, —NR$^{10}$—, or a covalent bond;

W is N or CR$^{10}$;

R$^5$ is one of hydrogen, C$_{1-4}$ alkyl, C$_{2-10}$ carboxyalkyl or C$_{2-10}$ hydroxyalkyl;

R$^6$, in each instance, is one of hydrogen, C$_{1-4}$ alkyl, hydroxy, C$_{1-4}$ alkoxy, phenoxy, C$_{1-4}$ alkyloxycarbonyl or cyano;

R$^7$ and R$^8$ are independently one of hydrogen, C$_{1-6}$ alkyl, C$_{2-10}$ carboxyalkyl or C$_{2-10}$ hydroxyalkyl, or R$^7$ and R$^8$ are taken together to form —(CH$_2$)$_y$— where y is 0, 1 or 2, provided that when W is N, y cannot be 0 or 1;

R$^9$ is hydrogen; or C$^{1-10}$ alkyl, optionally substituted with amino, mono(C$_{1-4}$)alkylamino, C$_{1-6}$ alkoxy, hydroxy, carboxy, phenyl, alkyloxycarbonyl, aralkoxycarbonyl, C$_{1-6}$ acylamino, cyano or trifluoromethyl;

R$^{10}$, in each instance, is independently hydrogen, C$_{1-6}$ alkyl, benzyl, phenyl, C$_{2-10}$ hydroxyalkyl, C$_{2-10}$ aminoalkyl, C$_{1-4}$ monoalkylamino(C$_{2-8}$)alkyl, C$_{1-4}$ dialkylamino(C$_{2-8}$)alkyl or C$_{2-10}$ carboxyalkyl;

R' is one of hydrogen, $C_{1-6}$ alkyl, $C_{3-8}$ cycloalkyl, phenyl, benzyl, trifluoromethyl, halogen, hydroxy($C_{1-8}$)alkyl, cyano, nitro, carboxamide, carboxy, alkoxycarbonyl, alkoxymethyl or alkoxy;

n is from zero to 8, with the proviso that when W is N, then n is from 2 to 8; and m is from 1 to 4, provided that when W is N, then m is not 1.

An especially preferred group of compounds include compounds of Formulae I–III wherein:

Z is one of $-SO_2O-$, $-SO_2NR^{10}-$, $-CH_2O-$ or $-OCH_2-$;

$R^1$ is one of phenyl or naphthyl, optionally substituted by one or two of chloro or dimethylamino;

$R^2$ and $R^3$ are each hydrogen or $R^2$ and $R^3$ may also be taken together to form $-CH=CH-CH=CH-$;

$R^4$ is one of hydrogen, methyl, methoxy or trifluoromethyl;

Y is one of O or $NR^{10}$;

W is N or $CR^{10}$;

$R^5$ is one of hydrogen, $C_{1-6}$ alkyl, $C_{2-10}$ hydroxyalkyl or $C_{2-10}$ carboxyalkyl;

$R^6$, in each instance is hydrogen or hydroxy;

$R^7$ and $R^8$ are independently one of hydrogen, $C_{1-6}$ alkyl, $C_{2-10}$ hydroxyalkyl or $C_{2-10}$ carboxyalkyl, or $R^7$ and $R^8$ are taken together to form $-(CH_2)_y-$, where y is zero, 1 or 2, with the proviso that when W is N, y cannot be zero or 1;

$R^9$ is hydrogen or $C_{1-4}$ alkyl;

$R^{10}$, in each instance, is independently hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$)alkyl, methylamino($C_{2-8}$)alkyl;

R' is hydrogen, methyl, methoxy or trifluoromethyl;

n is from zero to 4, with the proviso that when W is N, then n is 2 to 4; and m is 1,2 or 3.

Useful compounds falling within the scope of Formula I include compounds having one of Formulae IV–VI:

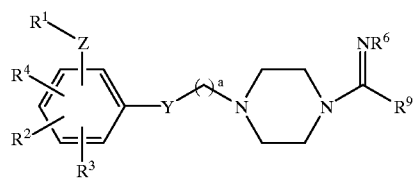

IV

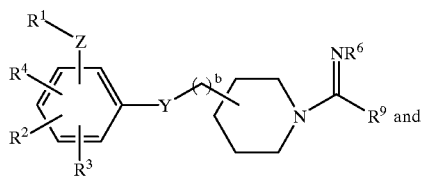

V

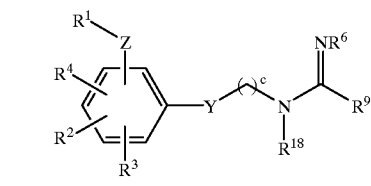

VI or solvates, hydrates or pharmaceutically acceptable salts thereof; wherein:

Z, $R^1$, $R^2$, $R^3$, $R^4$, Y, $R^6$, $R^9$ and $R^{10}$ are defined as above for Formulae I–III;

$R^{18}$ is one of hydrogen, alkyl, aralkyl, aryl, $C_{2-10}$ hydroxyalkyl or $C_{2-10}$ carboxyalkyl;

a is from 1 to 8, provided that when Y is other than $-CHR^{10}-$, then a is from 2 to 8;

b is from 1 to 8; and c is from 1 to 13, provided that when Y is other than $-CHR^{10}-$, then c is from 2–13.

Preferred compounds falling within the scope of Formula II include compounds having one of Formulae VII–IX:

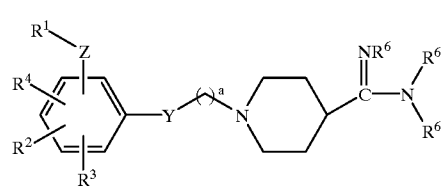

VII

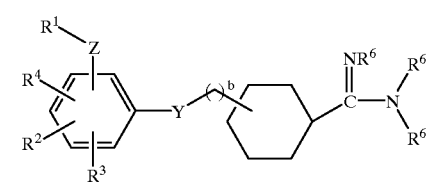

VIII

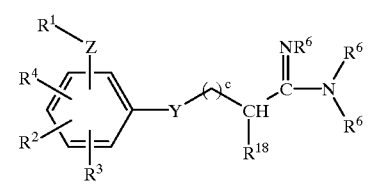

IX or solvates, hydrates or pharmaceutically acceptable salts thereof; wherein:

Z, $R^1$, $R^2$, $R^3$, $R^4$, Y, $R^6$, $R^9$ and $R^{10}$ are defined as above for Formulae I–III;

$R^{18}$ is one of hydrogen, alky, aralkyl, aryl, $C_{2-10}$ hydroxyalkyl or $C_{2-10}$ carboxyalkyl;

a is from 1 to 8, provided that when Y is other than $-CHR^{10}-$, then a is from 2 to 8;

b is from 1 to 8; and c is from 1 to 13, provided that when Y is other than $-CHR^{10}-$, then c is from 2–13.

Preferred compounds falling within the scope of Formula III include compounds having one of Formulae X or XI:

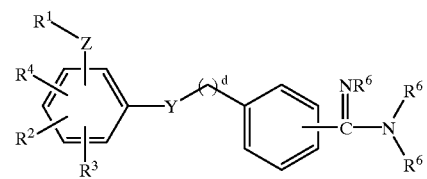

X

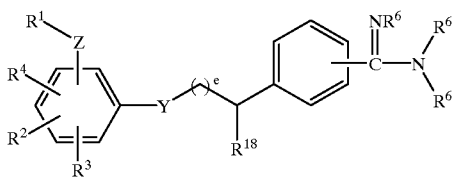

or solvates, hydrates or pharmaceutically acceptable salts thereof; wherein:

Z, $R^1$, $R^2$, $R^3$, $R^4$, Y, $R^6$, $R^9$ and $R^{10}$ are defined as above for Formulae I–III;

$R^{18}$ is one of alkyl aralkyl, aryl, $C_{2-10}$ hydroxyalkyl or $C_{2-10}$ carboxyalkyl;

d is from 1 to 8; and e is from 1 to 8.

The moiety —Z—$R^1$ of Formulae I–XI is attached to the benzene ring in a position ortho-, meta- or para- to Y.

The amidino moiety (—C(=$NR^6$)$NR^6R^6$) of Formulae III, X and XI can be attached in the ortho-, meta- or para-positions.

Preferred compounds of the present invention are those of Formula I–XI wherein Y is one of divalent oxygen (—O—) or —$NR^{10}$— and Z is one of —$SO_2NR^{10}$—, —$SO_2O$— or —$CH_2O$—.

Preferred compounds of the present invention are those of Formula I–XI wherein $R^1$ is one of $C_{1-12}$ alkyl, $C_{4-7}$ cycloalkyl, $C_{2-8}$ alkenyl, $C_{2-8}$ alkynyl or $C_{6-14}$ aryl, especially $C_{6-10}$ aryl, any of which is optionally substituted. Substituents that can be optionally present on the $R^1$ moieties include one or more, preferably one or two, hydroxy, nitro, trifluoromethyl, halogen, alkoxy, aminoalkoxy, aminoalkyl, hydroxyalkyl, hydroxyalkoxy, cyano, amino, monoalkylamino, dialkylamino, carboxy, carboxyalkyl, carboxyalkoxy, mono(hydroxyalkyl)amino, di(hydroxyalkyl)amino, mono(carboxyalkyl)amino, di(carboxyalkyl)amino, alkoxycarbonylamino, alkoxycarbonyl, aralkoxycarbonyl, alkenylcarbonyl, alkynylcarbonyl, alkylsulfonyl, alkenylsulfonyl, alkynylsulfonyl, alkylsulfinyl, alkylsulfonamido, amidino, guanidino, alkyliminoamino, formyliminoamino, trifluoromethoxy or perfluoroethoxy. A further substituent on aryl, cycloalkyl, alkenyl, alkynyl and aralkyl moities of $R^1$ includes one or more, preferably one or two, alkyl moieties. Preferred values of optional substituents on $R^1$ include hydroxy, nitro, trifluoromethyl, halogen, $C_{1-6}$ alkyl, $C_{1-6}$ alkoxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-10}$ mono(carboxyalkyl)amino, di($C_{2-10}$ carboxyalkyl)amino, $C_{6-14}$ ar($C_{1-6}$ alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{1-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, carboxyalkylamino, cyano, trifluoromethoxy, and perfluoroethoxy.

An additional preferred group of compounds are those compounds of Formulae I–XI wherein $R^1$ is heteroaryl or substituted heteroaryl. Preferred $R^1$ heteroaryl groups include pyridyl, thienyl, chromenyl, benzoxazolyl, quinazolinyl, quinolinyl and tetrahydroquinolinyl, with pyridyl, quinazolinyl, quinolinyl and tetrahydroquinolinyl being most preferred. Preferred compounds when $R^1$ is substituted heteroaryl include those compounds having one of the heteroaryl groups mentioned as preferred that have one or more, preferably one or two, substituents that are listed in the preceding paragraph.

Useful values of $R^1$ include phenyl, chlorophenyl, iodophenyl, dichlorophenyl, bromophenyl, trifluoromethylphenyl, di(trifluoromethyl)phenyl, methylphenyl, t-butylphenyl, methoxyphenyl, dimethoxyphenyl, hydroxyphenyl, carboxyphenyl, aminophenyl, methylaminophenyl, n-butylaminophenyl, amidinophenyl, guanidinophenyl, formyliminoaminophenyl, acetimidoylaminophenyl, methoxycarbonylphenyl, ethoxycarbonylphenyl, carboxymethoxyphenyl, naphthyl, hydroxynaphthyl, cyclohexyl, cyclopentyl, 2-propylbutyl, quinolinyl and tetrahydroquinolinyl.

The groups $R^2$, $R^3$ and $R^4$ in Formulae I–XI substitute for any remaining hydrogen atoms on the benzene ring after allowing for attachment of the moiety —Z—$R^1$. Preferred compounds are those where $R^2$, $R^3$ and $R^4$ are independently hydrogen, $C_{1-4}$ alkyl, $C_{4-7}$ cycloalkyl, $C_{6-14}$ aryl, especially $C_{6-10}$ aryl, $C_{6-10}$ ar($C_{1-4}$)alkyl, trifluoromethyl, halogen, hydroxyalkyl, cyano, nitro, carboxamide, carboxy, alkoxycarbonyl, carboxymethyl, alkoxycarbonylmethyl, or cycloalkyloxycarbonyl. Alternatively, $R^2$ and $R^3$, when attached to adjacent carbon atoms on the benzene ring, are one of —CH=CH—CH=CH— or —$(CH_2)_q$—, where q is from 2 to 6, thereby forming a fused ring. Preferred values of $R^2$ together with $R^3$ include —CH=CH—CH=CH—, —$CH_2$—$CH_2$—$CH_2$— and —$CH_2$—$CH_2$—$CH_2$—$CH_2$—. When $R^2$ and $R^3$ together form a fused ring, $R^4$ is preferably hydrogen.

Useful values of $R^2$, $R^3$ and $R^4$ include hydrogen, methyl, ethyl, chloro, bromo, trifluoromethyl, hydroxymethyl, methoxy, ethoxy, carboxamide, nitro, phenyl, cyclopropyl, hydroxy, isopropyl, methoxycarbonyl, ethoxycarbonyl and benzyl. Useful values of $R^2$, $R^3$ and $R^4$ also include $R^2$ and $R^3$ together forming —CH=CH—CH=CH or —$CH_2$—$CH_2$—$CH_2$— and $R^4$ being hydrogen.

Preferred values of $R^6$ in Formulae I–XI are hydrogen, hydroxy, $C_{1-6}$ alkyl, $C_{1-6}$ alkoxy, cyano or —$CO_2R^w$, where $R^w$, in each instance, is preferably one of $C_{1-4}$ alkyl or $C_{4-7}$ cycloalkyl. Suitable values of $R^6$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$. In the most preferred embodiments, each $R^6$ is hydrogen.

Preferred compounds include compounds of Formulae I and II, where $R^7$ and $R^8$ are independently one of hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl, or $R^7$ and $R^8$ are taken together to form —$(CH_2)_y$—, where y is most preferably 2. Useful values of $R^7$ and $R^8$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl.

Preferred compounds are those of Formulae I, IV, V and VI, wherein $R^9$ is $C_{1-10}$ hydrogen or alkyl optionally substituted by one, two or three of, preferably one of, amino, monoalkylamino, dialkylamino, alkoxy, hydroxy, alkoxycarbonyl, aryloxycarbonly, aralkoxycarbonyl, carboalkoxy, phenyl, cyano, trifluoromethyl, acetylamino, pyridyl, thienyl, furyl, pyrrolyl or imidazolyl.

Suitable values of $R^9$ include hydrogen, methyl, ethyl, propyl, n-butyl, benzyl, phenethyl, 2-hydroxyethyl, 3-hydroxypropyl, 4-hydroxybutyl, carboxymethyl and carboxyethyl.

Preferred values of $R^{10}$ in Formulae I–XI include hydrogen, $C_{1-6}$ alkyl, $C_{6-10}$ ar($C_{1-6}$)alkyl, $C_{6-10}$ aryl, $C_{2-10}$ hydroxyalkyl $C_{2-10}$ aminoalkyl, $C_{2-7}$ carboxyalkyl, mono ($C_{1-4}$ alkyl)amino($C_{1-8}$)alkyl, and di($C_{1-4}$ alkyl)amino ($C_{1-8}$)alkyl. Suitable values of $R^{10}$ include methyl, ethyl, propyl, n-butyl, benzyl, phenylethyl, 2-hydroxyethyl, 3-hydroxypropyl, 4-hydroxybutyl, 2-aminoethyl, 2-carboxymethyl, 3-carboxyethyl, 4-carboxypropyl and 2-(dimethylamino)ethyl.

Preferred values of n in Formulae I–III include from 1 to 6, more preferably from 1 to 4, and most preferably 1 or 2, with the proviso that when W is N and Y is other than —$CHR^{10}$—, then n is not 1. Preferred values of m include from 1 to 4, more preferably 1, 2 or 3, provided that when W is N, then m is not 1.

Preferred values of $R^5$ in Formula III include is one of hydrogen, $C_{1-4}$ alkyl, phenyl, benzyl, phenethyl, $C_{2-10}$ carboxyalkyl and $C_{2-10}$ hydroxyalkyl. Especially preferred values are hydrogen, $C_{1-6}$ alkyl, $C_{2-10}$ hydroxyalkyl and $C_{2-10}$ carboxyalkyl. Suitable values of $R^5$ include hydrogen, methyl, hydroxymethyl, hydroxyethyl, carboxymethyl and carboxyethyl.

Preferred values of R' in Formula III include hydrogen, $C_{1-6}$ alkyl, $C_{3-8}$ cycloalkyl, phenyl, benzyl, trifluoromethyl, halogen, hydroxy($C_{1-8}$)alkyl, cyano, nitro, carboxamide, carboxy, alkoxycarbonyl, alkoxymethyl and alkoxy. Suitable values of R' include hydrogen, methyl, methoxy and trifluoromethyl.

Preferred values of "a" in Formulae IV and VII include from 1 to 6, more preferably from 1 to 4, and most preferably 1 or 2, with the proviso that when Y is other than —$CHR^{10}$—, then n is not 1.

Preferred values of "b" in Formulae V and VIII include from 1 to 6, preferably from 1 to 4, and most preferably 1 or 2.

Preferred values of "c" in Formulae VI and IX include from 1 to 8, more preferably from 1 to 6, and most preferably 1, 2, 3, or 4.

Preferred values of "d" and "e" in Formulae V and XI include from 1 to 6, preferably from 1 to 4, and most preferably 1 or 2.

Preferred compounds of Formulae VI, IX and XI are those where $R^{18}$ is independently one of hydrogen, $C_{1-6}$ alkyl, $C_{6-10}$ ar($C_{1-6}$)alkyl, $C_{6-10}$ aryl, $C_{2-10}$ hydroxyalkyl and $C_{2-7}$ carboxyalkyl. Useful values of $R^{18}$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl. Most preferred compounds are those where $R^{18}$ is hydrogen.

Specific compounds within the scope of the invention include the following examples:

2-chlorobenzenesulfonic acid 3-[(1-acetimidoylpiperidin-4-yl)methoxy]-5-methylphenyl ester hydrochloride;

3-(2-chlorobenzyloxy)-5-methyl-1-[2-(1-acetimidoyl) piperazin-4-yl]]ethoxybenzene diacetic acid salt;

N-[2-(N,N-dimethylamino)ethyl]-N-[2-[[4-(1-acetimidoyl)amino]butoxy]-4-methylphenyl] benzenesulfonamide dihydrochloride;

N-benzyl-N-[[[3-(1-acetimidoyl)piperidin-4-yl] methylamino]phenyl]-benzenesulfonamide;

3-chlorobenzenesulfonic acid 3-[[(1-acetimidoyl) piperidin-4-yl]methoxy]-5-methylphenyl ester hydrochloride;

2-chlorobenzenesulfonic acid 3-[(3-amidinophenyl) methoxy]-5-methylphenyl ester hydrochloride;

2-chlorobenzenesulfonic acid 3-[[3-(N-hydroxy) amidinophenyl]methoxy]-5-methylphenyl ester hydrochloride;

2,3-dichlorobenzenesulfonic acid 3-[[(1-acetimidoyl) piperidin-4-yl]methoxy]-5-methylphenyl ester hydrochloride;

2-chloro-N-[[3-[(1-acetimidoyl)piperidin-4-yl]methoxy]-5-trifluoromethylphenyl]benzenesulfonamide hydrochloride;

2chloro-N-(5-carboxypentyl)-N-[[3-[(1-acetimidoyl) piperidin4-yl]methoxy]-5-trifluoromethylphenyl] benzenesulfonamide;

1-(5-(N,N-dimethylamino)naphthalenesulfonic acid 3-[[(1-acetimidoyl)piperidin-3-yl]methoxy]-5-methoxyphenyl ester hydrochloride;

2-chlorobenzenesulfonic acid 1-[[(1-acetimidoyl) piperidin-4-yl]methoxy]naphthalen-3-yl ester acetic acid salt;

3-[(2-chlorophenoxy)methyl]-[[(1-acetimidoyl)piperidin-4-yl]methoxy]benzene acetic acid salt;

2-Chlorobenzenesulfonic acid 3-[(4-amidinophenyl) methoxy]-5-methylphenyl ester hydrochloride;

2-chlorobenzenesulfonic acid 3-[(3-amidinophenyl) methoxy]phenyl ester hydrochloride;

2-chlorobenzenesulfonic acid 3-[5-amidinopentyloxy]-5-methylphenyl ester acetic acid salt;

2-chlorobenzenesulfonic acid 3-[3-amidinopropoxy]-5-methylphenyl ester hydrochloride; and 2-chlorobenzenesulfonic acid 3-[[3-(N-methylamidino) phenyl]methoxy]-5-methylphenyl ester hydrochloride.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The compounds of Formulae I–XI may also be solvated, especially hydrated. Hydration may occur during manufacturing of the compounds or compositions comprising the compounds, or the hydration may occur over time due to the hygroscopic nature of the compounds.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolinyl, tetrahydroquinolinyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$ alkyl groups having an aryl substituent, such as benzyl, phenylethyl or 2-naphthylmethyl.

The term "cycloalkyl" as employed herein by itself or as part of another group refers to cycloalkyl groups containing 3 to 9 carbon atoms, preferably 4 to 7 carbon atoms. Typical examples are cyclopropyl, cyclobutyl, cyclopentyl, cyclohexyl, cycloheptyl, cyclooctyl and cyclononyl.

The term "halogen" or "halo" as employed herein by itself or as part of another group refers to chlorine, bromine, fluorine or iodine with chlorine being preferred.

Scheme Ia illustrates but is not limited to the preparation of compounds of Examples 1, 5, 8, 9, 11, and 12.

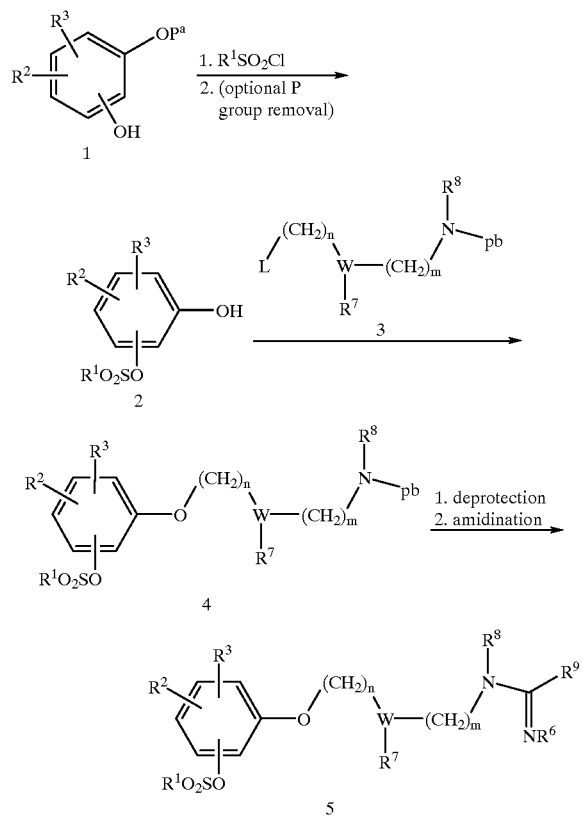

Each of $R^1$ through $R^3$, $R^6$ through $R^9$, n and m is as defined above; $P^a$ is a hydroxyl protecting group or hydrogen, and $P^b$ is an amino protecting group.

Phenols 1 (where P is H) are converted to monosulfonates 2 by treatment with appropriate sulfonyl chlorides. Preferred conditions include treating phenol 1 with a sulfonyl chloride in a biphasic system composed of ether and an aqueous phase saturated with $NaHCO_3$. Alternatively, the reaction may be effected first by deprotonating 1 with a strong base, most preferably NaH, in a polar organic solvent, such as DMF or tetrahydrofuran, followed by treating the deprotonated phenol with the sulfonyl chloride. Still alternatively, phenol 1, in a typical organic solvent, such as methylene chloride, may be converted to 2 by treating the phenol with sulfonyl chloride in the presence of an amine base, such as N-methylmorpholine.

Phenols 1 may be monoprotected ($P^a$ is a protecting group) with a variety of protecting groups known in the art, such as esters and benzyl ethers (Green, T. W. & Wuts, P. G. M., *Protective Groups in Organic Synthesis*, 2nd edition, John Wiley and Sons, Inc., New York (1991)). Deprotection of the hydroxyl groups is routinely accomplished using reaction conditions well-known in the art. For example, deprotection of benzyl ethers may be effected through catalytic hydrogenation using palladium on carbon as a catalyst.in solvents such as ethanol or tetrahydrofuran. Deprotection of an acetate is accomplished by basic hydrolysis, most preferably with sodium hydroxide in aqueous tetrahydrofuran.

Phenols 2 are coupled to 3 (for L=OH) using a Mitsunobu coupling procedure (Mitsunobu, O., *Synthesis* 1 (1981)) to provide 4. Preferred coupling conditions include using a trialkylphosphine or triarylphosphine, such as triphenylphosphine, in a suitable solvent such as tetrahydrofuran or methylene chloride, and a dialkyl azodicarboxylate, such as diethyl azodicarboxylate. In some cases, it is advantageous to add an amine is base such as N-methylmorpholine. The amine terminus of 3 is protected with a protecting group $P^b$ that is readily removed from 4. Amino-protecting groups are well known in the art (Greene, T. W. & Wuts, P.G.M., *Protective Groups in Organic Synthesis*, 2nd edition, John Wiley and Sons, Inc., New York (1991)). Deprotection of the amino group is effected by employing reaction conditions that are well known in the art. For example, the t-butoxycarbonyl (BOC) may be removed by exposure to strongly acidic medium, such as hydrogen chloride, in a suitable solvent, such as dioxane, or a mixed trifluoroacetic acid/methylene chloride solvent system. Benzyloxycarbonyl (CBz) groups may be removed by hydrogen using palladium on carbon as a catalyst in solvents such as ethanol or tetrahydrofuran. The resulting amine is then converted to amidine 5 in a manner similar to the procedure described by Nagahara et. aL, *J. Med. Chem.* 37(8):1200–1207 (1994) wherein the amine is treated with an appropriate imidate in the presence of a base such as N,N-diisopropylethylamine in an appropriate solvent such as DMF. Alternatively, the amine is treated with an appropriate imidate in the presence of a base, such as sodium hydroxide, in an appropriate solvent, such as methanol.

Scheme Ib illustrates but is not limited to the preparation of compounds of Examples 2 and 13.

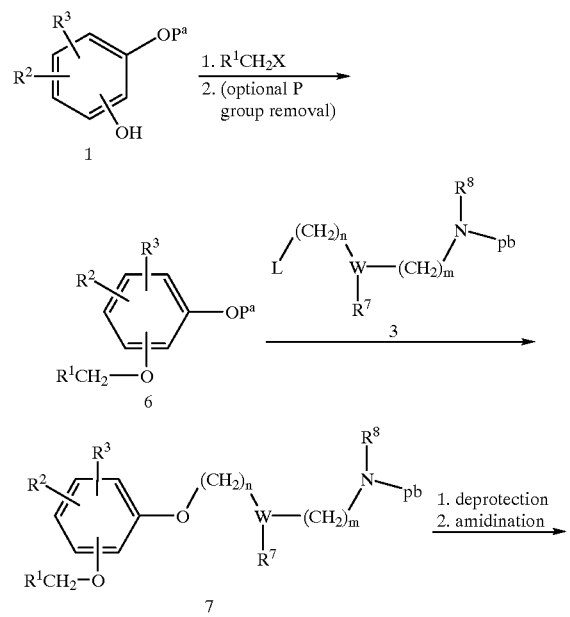

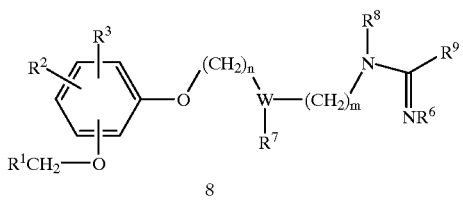

8

$R^1-R^3$, $R^6-R^8$, n, m $P^a$ and $P^b$ are each as defined above.

Aryl ethers 8 are synthesized in a fashion analogous to synthesis of 5. Phenol 1 (P is H) is converted to derivative 6 by treating 1 with a strong base, preferably NaH, in a suitable solvent such as DMF, followed by addition of a reactive alkyl or benzyl compound, $R^1CH_2X$ (where X is a reactive functional group such as iodide, chloride, bromide or alkylsulfonate). Alternatively, the Mitsunobu Reaction may be used with an appropriate $R^1CH_2X$ (X=OH) using the reaction conditions described above. The use of suitable alcohol protecting groups ($P^a$), such as esters, to suppress over-alkylation, is well known in the art (Greene, T. W. & Wuts, P.G.M., *Protective Groups in Organic Synthysis*, 2nd edition, John Wiley and Sons, Inc., New York (1991)). The protecting group may then be removed using well-known techniques, for example by hydrolysis with aqueous NaOH, when an ester protecting group is employed. Phenol 6 is then converted to amidine 8 using the conditions described for formation of 5.

Scheme II illustrates, but is not limited to, the preparation of compounds exemplified by Examples 3, 9 and 10.

Scheme II

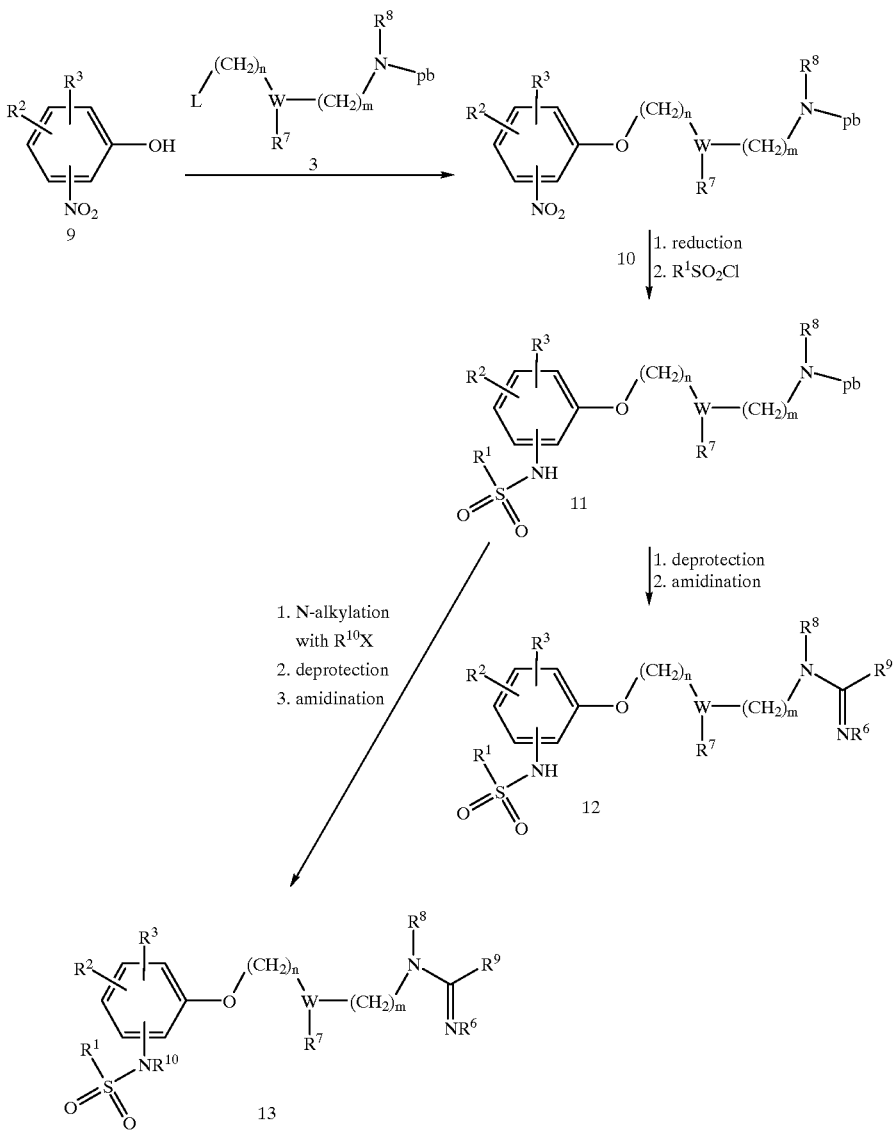

$R^1-R^3$, $R^6-R^{10}$, n, m, $P^a$ and $P^b$ are as defined above.

According to Scheme II, a nitrophenol 9 may be coupled to compound 3 by standard techniques. Preferably, the reaction is effected by the Mitsunobu reaction (where L is OH). Alternatively, 9 may be treated with a base, such as NaH, in a suitable solvent such as DMF or THF, followed by addition of 3 (where L is a reactive group, such as Cl, Br, I or alkylsulfonate). The nitro group is thereafter reduced, for example, by catalytic reduction using palladium on carbon in a suitable solvent such as ethanol or tetrahydrofuran. The resulting product in then treated with an appropriate sulfonyl chloride ($R^1SO_2Cl$) to provide 11. Removal of the amine protecting group $P^b$ is accomplished by techniques known in the art. For example, the t-butoxycarbonyl (BOC) is removed by exposure to a strongly acidic medium, such as hydrogen chloride in a suitable solvent such as dioxane or trifluoroacetic acid in methylene chloride. Benzyloxycarbonyl (CBz) groups are removed by catalytic hydrogen using palladium on carbon as a catalyst in solvents such as ethanol or tetrahydrofuran.

The resulting amine is then converted to amidine 12 in a manner similar to the procedure described by Nagahara et. al., *J. Med. Chem.* 37(8):1200–1207 (1994) wherein the amine is treated with an appropriate imidate in the presence of a base such as N,N-diisopropylethyl amine in an appropriate solvent such as DMF. Alternatively, the amine is treated with an appropriate imidate in the presence of a base such as sodium hydroxide as base in an appropriate solvent such as methanol. N-Substituted sulfonamide derivative 13 is obtained by alkylation of 11 employing a suitable alkylating agent ($R^{10}X$) in the presence of a base, most preferably $Cs_2CO_3$ using a polar solvent such as DMF. Deprotection and amidination are then executed in a manner similar to the conversion of 11 to 12.

Scheme III illustrates but is not limited to the preparation of compounds of Example 4.

Scheme III

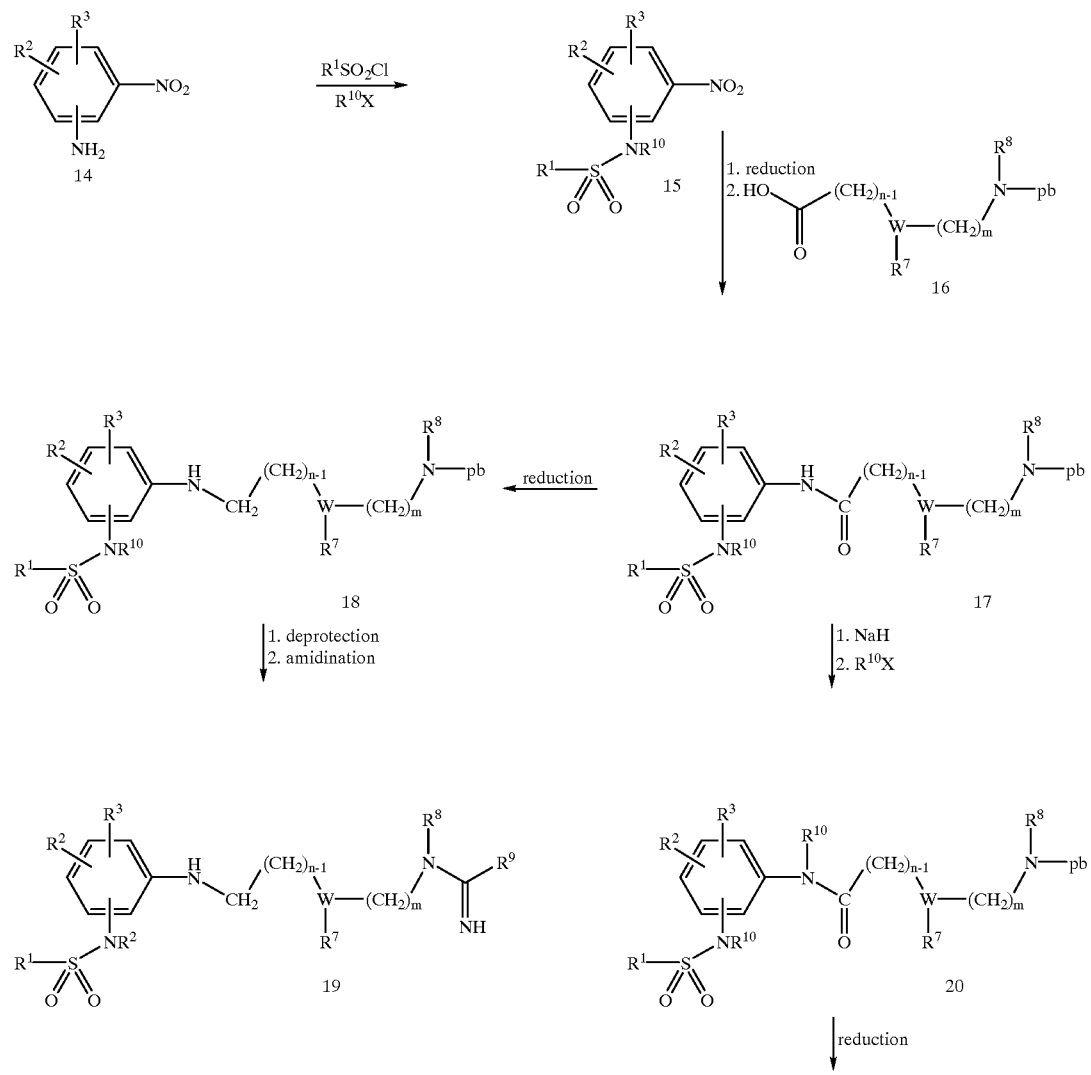

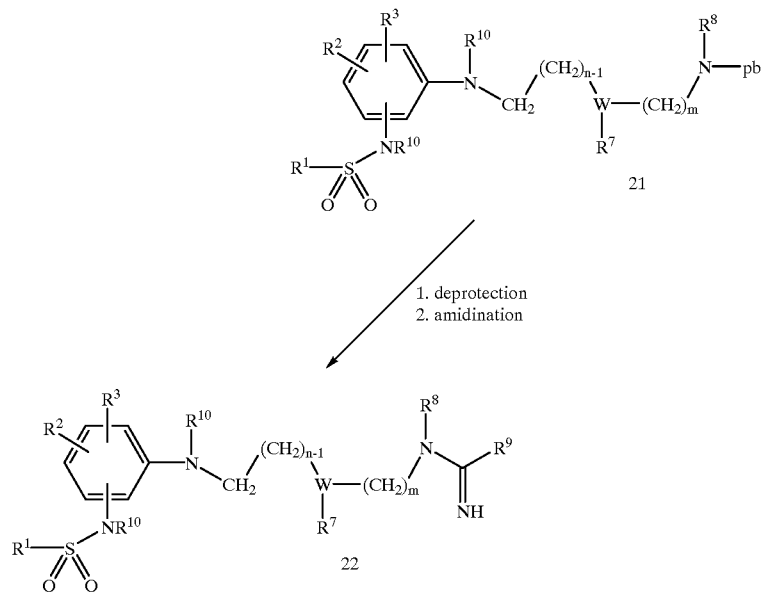

21

1. deprotection
2. amidination

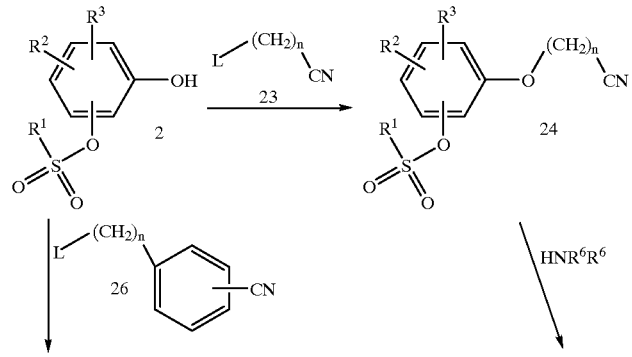

22

$R^1$–$R^3$, $R^7$–$R^{10}$, n, m and $P^b$ are each as defined above.

According to Scheme III, nitroaniline 14 is converted to a sulfonamide by treatment with an appropriate sulfonyl chloride $R^1SO_2Cl$ in the presence of a weak base, such as N-methylmorpholine. The resulting sulfonamide nitrogen is alkylated with a suitable alkylating agent ($R^{10}X$) in the presence of a base, preferably an alkali metal carbonate such as $Cs_2CO_3$ or $K_2CO_3$, using a polar solvent, such as DMF, to provide intermediate 15. After reduction of the nitro group, the resulting aniline is coupled to a carboxylic acid, 16, to provide amide 17. Amide coupling may be performed using any of a number of common peptide coupling reagents. Preferably, one of 1,3-dicyclohexylcarbodiimide or Castro's reagent (BOP) are employed (B. Castro et al., *Tetrahedron Lett.*: 1219 (1975)). Alternatively, 17 may be formed by coupling the aniline with the corresponding acid chloride of acid 16 in the presence of an acid scavenger, such as N-methylmorpholine. Amide 17 is converted to amine 18 by reduction of the amide functionality with an appropriate hydride reagent, preferably borane-THF complex or chlorotrimethylsilane and lithium borohydride. This reaction occurs in a suitable polar solvent, such as THF. Removal of the amine protecting group $P^b$ and formation of the amidine as described in Scheme II provides the desired compound 19. Alternatively the amide nitrogen may be alkylated using a strong base, such as sodium hydride, in a suitable polar solvent such as DMF, followed by treatment with an alkylating agent ($R^{10}X$) to afford intermediate 20. Reduction of the amide, as executed in the formation of 18, to give 21 followed by deprotection and amidination as previously described provides the analogous compound 22.

Scheme IV illustrates but is not limited to the preparation of compounds of Examples 6, 7, 14, 15, 16, 17 and 18.

Scheme IV

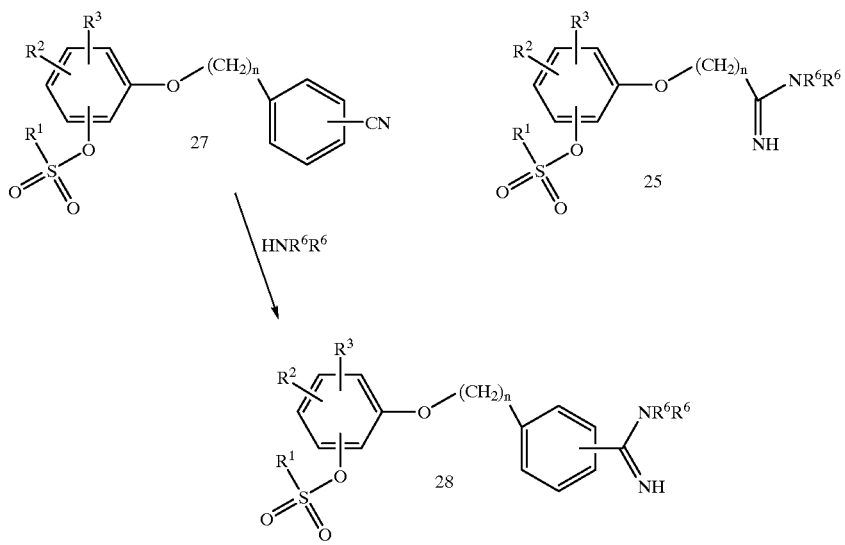

$R^1$–$R^3$, $R^6$ and n are each as defined above.

Monosulfonates 2 are converted to cyano derivatives 24 by exposing 2 to a base, most preferably sodium hydride in a suitable solvent such as DMF, followed by addition 23, where L is a reactive group such as iodide, chloride, bromide, alkyl sulfonate, or aryl sulfonate. Alternatively, the Mitsunobu Reaction may be used with an appropriate alcohol 23, where L=OH. The nitrite is submitted to amidino formation conditions such as those described by Nagahara et. al., *J. Med. Chem.* 37(8):1200–1207 (1994), wherein the nitrile is first exposed to a strong acid, preferably hydrogen chloride, in a suitable alcoholic solvent, preferably methanol or ethanol, which converts the nitrile to an imidate. Following brief isolation, the imidate is treated with an appropriate amine $HNR^6R^6$ to effect formation of 25. Similarly, benzamidines 28 are prepared from 2 using appropriate benzonitrile derivatives 26.

It is to be understood that in each of the above-mentioned schemes, an additional substituent, $R^4$, may be present on the phenyl ring of the starting material.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of Formulae I–XI with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, cyclamic acid, pivalic acid and the like; useful inorganic acids are hydrohalide acids such as HCl, HBr, HI; sulfuric acid; phosphoric acid and the like. Preferred acids for forming acid addition salts include HCl and acetic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to inhibit trypsin-like proteases.

An end use application of the compounds that inhibit chymotrypsin and trypsin is in the treatment of pancreatitis. For their end-use application, the potency and other biochemical parameters of the enzyme-inhibiting characteristics of the compounds of the present invention is readily ascertained by standard biochemical techniques well-known in the art. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit either factor Xa or thrombin may be employed for a number of therapeutic purposes. As factor Xa or thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; hip replacement; and thrombus formation resulting from either thrombolytic therapy or percutaneous transluminal coronary angioplasty (PCTA). The compounds of the present invention may also be used as an anticoagulant in extracorporeal blood circuits.

By virtue of the effects of both factor Xa and thrombin on a host of cell types, such as smooth muscle cells, endothelial cells and neutrophils, the compounds of the present invention find additional use in the treatment or prophylaxis of adult respiratory distress syndrome; inflammatory responses, such as edema; reperfusion damage; atherosclerosis; and restenosis following an injury such as balloon angioplasty, atherectomy, and arterial stent placement.

The compounds of the present invention may be useful in treating neoplasia and metastasis as well as neurodegenerative diseases, such as Alzheimer's disease and Parkinson's disease.

When employed as thrombin or factor Xa inhibitors, the compounds of the present invention may be administered in an effective amount within the dosage range of about 0.1 to about 500 mg/kg, preferably between 0.1 to 10 mg/kg body weight, on a regimen in single or 2–4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

Human leucocyte elastase is released by polymorphonuclear leukocytes at sites of inflammation and thus is a contributing cause for a number of disease states. Thus, compounds of the present invention are expected to have an anti-inflammatory effect useful in the treatment of gout, rheumatoid arthritis and other inflammatory diseases, and in the treatment of emphysema. Cathepsin G has also been implicated in the disease states of arthritis, gout and emphysema, and in addition, glomerulonephritis and lung infestations caused by infections in the lung. In their end-use application the enzyme inhibitory properties of the compounds of Formulae I–XI is readily ascertained by standard biochemical techniques that are well-known in the art.

The neutrophil elastase inhibitory properites of compounds within the scope of the present invention are determined by the following method. Neutrophil elastase is prepared by the procedure described by Baugh et al., *Biochemistry* 15:836 (1979). Enzyme assays are conducted substantially according to the procedure disclosed by Nakajima et al., *J. Biol. Chem.* 254:4027 (1979), in assay mixtures containing 0.10 M Hepes (N-2-hydroxyethylpiperazine-N'-2-ethanesulfonic acid) buffer, pH 7.5; 0.5 M NaCl; 10% dimethylsulfoxide; and $1.50 \times 10^{-4}$ M MeOSuc-Ala-Ala-Pro-Val-p-nitroanilide as substrate. Inhibitors are evaluated by comparing enzymatic activity measured in the presence and absence of inhibitor.

The Cathepsin G inhibitory properties of compounds within the scope of the present invention are determined by the following method. A preparation of partially purified human Cathepsin G is obtained by the procedure of Baugh et al., *Biochemistry* 15:836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4° C. A protein fraction precipitates during dialysis and is isolated by centrifugation. This fraction contains most of the chymotrypsin-like activity of leukocyte granules. Specific substrates are prepared for each enzyme, namely MeOSuc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10 M Hepes buffer, pH 7.5, containing 0.50 M NaCl, 10% dimethylsulfoxide and 0.0020 M Suc-Ala-Ala-Pro-Phe-p-nitroanilide as a substrate. Hydrolysis of the p-nitroanilide substrate is monitored at 405 nm and at 25° C.

Useful dose range for the application of compounds of the present invention as neutrophil elastase inhibitors and as Cathepsin G inhibitors will of course depend upon the nature and severity of the disease state, as determined by the attending diagnostician, with the range of 0.01 to 10 mg/kg of body weight, per day, being useful for the aforementioned disease states.

Compounds of the present invention that inhibit urokinase or plasminogen activator are potentially useful in treating excessive cell growth disease state. As such the compounds of the present invention may also be useful in the treatment of benign prostatic hypertrophy and prostatic carcinoma, the treatment of psoriasis, and in their use as abortifacients. For their end-use application, the potency and other biochemical parameters of the enzyme inhibiting characteristics of the compounds of the present invention are readily ascertained by standard biochemical techniques well-known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of this assay by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

2-Chlorobenzenesulfonic Acid 3-[(1-Acetimidoylpiperidin4-yl)Methoxy]-5-Methylphenyl Ester Hydrochloride a) N-tert-Butoxycarbonylisonipecotic Acid Di-tert-butyl dicarbonate (6.55 g, 30 mmol) was added to the mixture of isonipecotic acid (3.90 g, 30 mmol) and $NaHCO_3$ (5.05 g, 60 mmol) in 1:1 1,4-dioxane/water (100 mL), and the mixture was stirred at room temperature overnight. The reaction mixture was evaporated in vacuo, acidified to pH 6 using 10% citric acid and extracted with ethyl acetate (3×100 mL). The organic phase was washed with brine (2×50 mL) and dried over $Na_2SO_4$. The solvent was evaporated to give the title compound as a white solid (6.25 g, 91%). $^1$H-NMR (300 MHz, $CDCl_3$) δ 1.43 (s, 9 H), 1.63 (m, 2 H), 1.88 (dd, 2 H, J=1.5, 6.6 Hz), 2.45 (m, 1 H), 2.83 (t, 2 H, J=11.4 Hz), and 4.00 (d,2 H, J=6.7 Hz).

b) N-tert-Butoxycarbonyl-4-piperidinemethanol

Borane-tetrahydrofuran (1 M, 25 mL, 25 mmol) was added slowly to N-tert-butoxycarbonylisonipecotic acid (5.73 g, 25 mmol), as prepared in the preceding step, in tetrahydrofuran (50 mL) at 0° C. (ice-bath) over 30 min. The mixture was stirred at 0° C. overnight and then warmed up to room temperature for 6 h. Water (10 mL) was added slowly and then $K_2CO_3$ (5 g in 50 mL water) was added. The mixture was extracted with ethyl acetate (3×50 mL). The organic phase was washed sequentially with saturated $NaHCO_3$ (2×50 mL) and brine (2×50 mL), and dried over $Na_2SO_4$. The solvent was removed in vacuo, and the residue was purified by flash column chromatography (1:1 hexane/ethyl acetate) to give the title compound as white crystals (4.55 g, 84%). $^1$H-NMR (300 MHz, $CDCl_3$) δ 1.13 (m, 2 H), 1.42 (s, 9 H), 1.67 (m, 4 H), 2.67 (t, 2 H, J=12.5 Hz), 3.46 (d, 2 H, J=3.0 Hz), and 4.09 (d, 2 H, J=3.6 Hz).

c) 2-Chlorobenzenesulfonic Acid 3-Hydroxy-5-methylphenyl Ester

Orcinol monohydrate (1.42 g, 10 mmol) and 2-chlorobenzenesulfonyl chloride (2.43 g, 11 mmol) were mixed in saturated $NaHCO_3$ (30 mL) and diethyl ether (30 mL). The biphasic mixture was stirred vigorously at room temperature for 2 days. The reaction mixture was quenched with 50 mL of water and extracted into ethyl acetate (3×50 mL). The organic phase was washed with brine (2×50 mL) and dried over $Na_2SO_4$. After removing the solvent in vacuo, the residue was purified by flash column chromatography (2% ethyl acetate in methylene chloride) to give the title compound as a pale-yellow liquid (2.15 g, 71%). $^1$H-NMR (300 MHz, $CDCl_3$) δ 2.22 (s, 3 H), 5.24 (s, 1 H), 6.43 (s, 1 H), 6.52 (s, 2H), 7.38 (m, 1 H), 7.60 (m, 2 H), and 7.96 (dd, 1 H, J=0.6, 3.9 Hz).

d) 2-Chlorobenzenesulfonic Acid 3-[[N-(tert-Butoxycarbonyl)piperidin4-yl[methoxy]-5-methylphenyl Ester Diethyl azodicarboxylate (349 mg, 2.0 mmol) was added to a solution of 2-chlorobenzenesulfonic acid 3-hydroxy-5-methylphenyl ester (600 mg, 2.0 mmol), as prepared in the preceding step, N-tert-butoxylcarbonyl4-piperidinemethanol (430 mg, 2.0 mmol), as prepared in step (b), and triphenylphosphine (525 mg, 2.0 mmol) in tetrahydrofuran (15 mL) at 0° C. The reaction mixture was stirred at 0° C. for 2 h and at room temperature for 3 h. The reaction mixture was quenched with water (50 mL) and was extracted with ethyl acetate (3×50 mL). The organic phase was washed with saturated $NaHCO_3$ (2×50 mL), brine (2×50 mL) and dried over $Na_2SO_4$. The solvent removed in vacuo and the residue was purified by flash column chromatography (2:1 ethyl acetate/hexane) to give the title compound as a colorless syrup (895 mg, 90%). $^1$H-NMR (300 MHz, CDCl$_3$) δ 1.24 (m, 2 H), 1.47 (s, 9 H), 1.76 (d, 2 H, J=6.6 Hz), 1.89 (m, 1 H), 2.24 (s, 3 H), 2.72 (t, 2 H, J=2.4 Hz), 3.68 (d, 2 H, J=3.2 Hz), 4.13 (m, 2 H), 6.47 (t, 1 H, J=2.2 Hz), 6.52 (d, 1 H, J=0.7 Hz), 6.58 (d, 1 H, J=0.8 Hz), 7.38 (dd, 1 H, J=0.6, 0.8 Hz), 7.61 (m, 2 H), and 7.97 (dd, 1 H, J=0.8, 4.0 Hz).

e) 2-Chlorobenzenesulfonic Acid 3-[(Piperidin4-yl)methoxy]-5-methylphenyl Ester

2-Chlorobenzenesulfonic acid 3-[[N-(tert-butoxycarbonyl)piperidin4-yl]methoxy]-5-methylphenyl ester (745 mg, 1.5 mmol), as prepared in the preceding step, was treated with 4 N HCl in 1,4-dioxane (20 mL) at room temperature for 2 h. The solvent was removed in vacuo and the residue was purified by flash column chromatography (10% methanol in methylene chloride saturated with NH$_3$) to give the title compound as a colorless syrup (570 mg, 95%). $^1$H-NMR (300 MHz, CDCl$_3$) δ 1.45 (m, 1 H), 1.94 (m, 3 H), 2.23 (s, 3 H), 2.45 (m, 1 H), 2.71 (dt, 2 H, J=1.2, 12.3 Hz), 3.51 (m, 2 H), 3.76 (m, 2 H), 6.46 (t, 1 H, J=2.1 Hz), 6.53 (s, 1 H), 6.58 (s, 1 H), 7.40 (t, 1 H, J=6.5 Hz), 7.62 (m, 2 H), and 7.97 (dd, 1 H, J=1.4, 7.9 Hz). Mass spectrum (MALDI-TOF, sinapinic acid matrix) calcd. for C$_{19}$H$_{22}$NO$_4$SCl: 396.1 (M+H), Found: 396.4.

f) 2-Chlorobenzenesulfonic Acid 3-[(1-Acetimidoylpiperidin4-yl)methoxy]-5-methylphenyl Ester Hydrochloride Triethylamine (0.5 mL) and ethyl acetimidate hydrochloride (247 mg, 2.0 mmol) were added to a solution of 2-chlorobenzenesulfonic acid 3-[(piperidin-4-yl)methoxy]-5-methylphenyl ester (396 mg, 1.0 mmol), as prepared in the preceding step, in N,N-dimethylformamide (10 mL). The reaction mixture was stirred at room temperature overnight. The N,N-dimethylformamide was removed in vacuo and the residue partitioned between methylene chloride (200 mL) and 10% K$_2$CO$_3$ (50 mL). The organic phase was washed with 10% K$_2$CO$_3$ (2×50 mL) and dried over K$_2$CO$_3$. The solvent was removed in vacuo, HCl-methanol (30 mL) was added, and the solution was concentrated in vacuo. The residue was crystallized from methanol-ethyl acetate to give the title compound as white crystals (405 mg, 86%). $^1$H-NMR (300 MHz, DMSO-d$_6$) δ 1.30 (m, 2 H), 1.82 (d, 2 H, J=7.0 Hz), 2.05 (m, 1 H), 2.20 (s, 3 H), 2.29 (s, 3 H), 3.16 (m, 2 H), 3.77 (d, 2 H, J=3.0 Hz), 3.92 (d, 1 H, J=6.5 Hz), 4.17 (d, 1 H, J=6.5 Hz), 6.46 (d, 1 H, J=2.5 Hz), 6.49 (s, 1 H), 7.59 (t, 1 H, J=8.0 Hz), 7.87 (m, 2 H), 7.95 (d, 1 H, J=8.0 Hz), 8.77 (br s, 1 H), and 9.35 (br s, 1 H). Mass spectrum (MALDI-TOF, sinapinic acid matrix) calcd. for C$_{21}$H$_{25}$N$_2$O$_4$SCl: 437.1 (M+H). Found: 436.8.

EXAMPLE 2

3-(2-Chlorobenzyloxy)-5-methyl-1-[2-(1-acetimidoyl)piperazin-4-yl]]ethoxybenzene Diacetic Acid Salt a) N-(tert-Butoxycarbonyl)-1-(2-hydroxyethyl)piperazine To a solution of 1-(2-hydroxyethyl)piperazine (5.20 g, 40 mmol) and triethylamine (6 mL 43 mmol), in 1,4-dioxane (100 mL) was added slowly di-tert-butyl dicarbonate (8.72 g, 40 mmol). The reaction mixture was stirred at room temperature for 2 h. The solvent was removed in vacuo and the residue was purified by flash column chromatography (ethyl acetate to 2% methanol in ethyl acetate) to give the title compound as colorless oil (8.32 g, 90%). $^1$H-NMR (300 MHz, CDCl$_3$) δ 1.46 (s, 9 H), 2.46 (t, 4 H), 2.55 (t, 2 H), 2.75 (br s,1 H), 3.44 (t, 4 H), and 3.63 (t, 2 H).

b) 3-(2-Chlorobenzyloxy)-5-methylphenol

To 1.31 g (9.22 mmol) of orcinol monohydrate in 20 mL anhydrous N,N-dimethylformamide under a nitrogen atmosphere was added 220 mg (9.17 mmol) of NaH (100%). After 5 min, 1.30 mL (10.0 mmol) of 2-chlorobenzyl bromide was added. The reaction mixture was stirred for 2 h and then quenched with 1 N HCl. The reaction mixture was extracted into ethyl acetate (200 mL). The organic phase was washed with water (4×100 mL), dried (MgSO$_4$), and concentrated in vacuo. Purification by flash chormatography (diethyl ether/hexane (50:50 to 100:0) gave 656 mg of the title compound as a glass. $^1$H-NMR (300 MHz, CDCl$_3$) δ 7.54 (dd, 1 H, J=3, 7 Hz), 7.39 (dd, 1 H, J=3, 7 Hz), 7.2–7.3 (m, 2 H), 6.41 (s, 1 H), 6.29–6.30 (m, 2 H), 5.29 (s, 2 H), and 2.28 (s, 3 H).

c) 3-(2-Chlorobenzyloxy)-5-methyl-1-[2-[N-(tert-butoxycarbonyl)piperazin-4-yl]]ethoxybenzene To a solution of 210 mg (0.845 mmol) of 3-(2-chlorobenzyloxy)-5-methylphenol as prepared in the preceding step, 204 mg (0.887 mmol) of N-(tert-butoxycarbonyl)-1-(2-hydroxyethyl)piperazine, as prepared in step (a) of this Example, 287 mg (1.10 mmol) of triphenylphosphine, and 280 µL (2.5 mmol) of N-methylmorpholine in 3 mL of tetrahydrofuran was added 160 µL (1.09 mmol) of N,N-diethyl azodicarboxylate. After stirring overnight at ambient temperature, the reaction mixture was quenched with water, extracted into ethyl acetate, dried (MgSO$_4$), and purified by flash chromatography (methylene chloride/diethyl ether (8:1 to 4:1)) to give the 270 mg (59% yield) of the title compound as a gum. $^1$H-NMR (300 MHz, CDCl$_3$) δ 7.55 (dd, 1 H), 7.37–7.41 (m, 1 H), 7.22–7.3 (m, 2 H), 6.43 (s, 1 H), 6.37 (d, 2 H), 5.12 (d, 2 H), 4.08 (t, 2 H, J=6.7 Hz), 3.45 (t, 4 H), 2.80 (t, 2 H, J=6 Hz), 2.51 (t, 4 H), and 1.46 (s, 9 H). Mass spectrum (MALDI-TOF; gentisic acid matrix) calcd. for C$_{25}$H$_{33}$ClN$_2$O$_4$: 461.2 (M+H). Found: 460.9.

d) 3-(2-Chlorobenzyloxy)-5-methyl-1-[2-[piperazin-4-yl]]ethoxybenzene Dihydrochloride A solution of 251 mg (0.544 mmol) of 3-(2-chlorobenzyloxy)-5-methyl-1-[2-[N-(tert-butoxycarbonyl)piperazin-4-yl]]ethoxybenzene as prepared in the preceding step, in 3 mL of methylene chloride and 500 δ of 4 N HCl in dioxane was stirred for 1 h. Another 1 mL of 4 N HCl in dioxane was added. After stirring for another 15 min, the reaction mixture was triturated with diethyl ether. The product was collected by filtration to provide 127 mg of the title compound as a colorless solid. $^1$H-NMR (300 MHz, DMSO-d$_6$) δ 9.50 (br s, 2 H), 7.58–6.61 (m, 1 H), 7.51–7.57 (m, 1 H), 7.37–7.40 (m, 2 H), 6.53 (s, 1 H), 6.49 (s, 3 H), 5.12 (s, 2 H), 4.35 (br s, 2 H), and 2.27 (s, 3 H). Mass spectrum (MALDI-TOF; α-cyano-4-hydroxycinnamic acid matrix) calcd. for C$_{20}$H$_{25}$ClN$_2$O$_2$: 361.2 (M+H). Found: 360.9.

e) 3-(2-Chlorobenzyloxy)-5-methyl-1-[2-[1-(acetymidoyl)piperazin4-yl]]ethoxybenzene Diacetic Acid Salt A solution of 104 mg (0.240 mmol) of 3-(2-chlorobenzyloxy)-5-methyl-1-2-[N-(tert-butoxycarbonyl)piperazin4-yl]]ethoxybenzene, as prepared in the preceding step, 90 mg (0.732 mmol) of ethyl acetimidate hydrochloride in 1 mL of N,N-dimethylformamide containing 260 µL of N,N-diisopropylethylamine was stirred at ambient temperature for 2 days. The solvent was removed in vacuo. The residue was quenched with 1 N sodium hydroxide, extracted into methylene chloride, dried (K$_2$CO$_3$), and concentrated. The residue was dissolved in 1 mL methylene chloride and then treated with 500 µL glacial acetic acid. The solution was then purified by preparative thin layer chromatography using methylene chloride/glacial acetic acid/methanol (53:13:34) as developing solvent to give 32.6 mg of the title compound as a colorless foam after repeated concentrations from diethyl ether/methylene chloride/hexane. $^1$H-NMR (300 MHz, DMSO-$d_6$) δ 9–9.0 (br s, 2 H), 7.50–7.60 (m, 2 H), 7.38–7.41 (m, 2 H), 6.48 (s, 1 H), 6.39 (s, 2 H), 5.11 (s, 2 H), 4.06 (t, 2 H), 3.53–3.56 (m, 4 H), 2.74 (t, 2 H), 2.60 (t, 4 H), 2.27 (s, 3 H), 2.24 (s, 3 H), and 1.85 (br s, 6 H). Mass spectrum (MALDI-TOF; α-cyano4-hydroxycinnamic acid matrix) calcd. for $C_{22}H_{28}ClN_3O_2$: 402.2 (M+H). Found: 401.8.

EXAMPLE 3

N-[2(N,N-Dimethylamino) ethyl]-N-[2-[[4-(1-acetimidoyl)amino]butoxyl-]4-methylphenyl]benzenesulfonamide Dihydrochloride.

a) 2-[(4-(tert-Butoxycarbonylamino)butoxy]4-methylnitrobenzene.

To 252 mg (1.33 mmol) 4-(tert-butoxycarbonylamino) butanol, 407 mg (2.66 mmol) 4-methyl-2-nitrophenol and 383 mg (1.46 mmol) triphenylphosphine in 1.0 mL of anhydrous tetrahydrofuran under nitrogen was added 336 μL (1.46 mmol) of diethyl azodicarboxylate. After stirring for 1 h, the mixture was concentrated to a yellow syrup. Chromatography on a Waters Associates 10 g silica Sep-Pak SPE column eluting with 10–12% ethyl acetate—hexane afforded 422 mg (98%) of the title compound as a colorless oil. $^1$H-NMR (300 MHz, CDCl$_3$) δ 7.64 (d, 1 H, J=2.0 Hz), 7.30 (dd, 1 H, J=8.5, 2.2 Hz), 6.95 (d, 1 H, J=8.5 Hz), 4.64 (br s, 1 H), 4.09 (t, 2 H, J=6.1 Hz), 3.19 (q, 2H, J=6.5 Hz), 2.34 (s, 3 H), 1.86 (m, 2 H), 1.69 (m, 2 H), and 1.44 (s, 9 H). Mass spectrum (MALDI-TOF, gentisic acid matrix) calcd. for $C_{16}H_{24}N_2O_5$: 347.2 (M+H). Found: 347.3.

b) 2-[(4-(tert-Butoxycarbonylamino)butoxy]-4-methylaniline.

To a solution of 390 mg (1.20 mmol) of 2-[(4-(tert-butoxycarbonylamino) butoxy]-4-methylnitrobenzene, as prepared in preceding step, in 1.5 mL of tetrahydrofuran was added 39 mg of 10% palladium on carbon and the mixture stirred under a balloon of hydrogen for 20 h. The mixture was filtered (Celite) washing with 3 mL of tetrahydrofuran and concentrated to 339 mg (96%) of the title compound as a colorless oil. $^1$H-NMR (300 MHz, CDCl$_3$) δ 6.66 (d, 1 H, J=8.0 Hz), 6.55 (dd, 1 H, J=2.0 Hz), 6.49 (d, 1 H, J=8.0 Hz), 4.59 (br s, 1 H), 3.98 (t, 2 H, J=6.3 Hz), 3.19 (q, 2 H, J=6.6 Hz), 2.21 (s, 3 H), 1.82 (m, 2 H), 1.67 (m, 2 H), 1.57 (br s, 2 H), and 1.44 (s, 9 H). Mass spectrum (MALDI-TOF, gentisic acid matrix) calcd. for $C_{16}H_{26}N_2O_3$: 317.2 (M+Na). Found: 317.2.

c) N-[2-[4-(tert-Butoxycarbonylamino)-butoxy]-4-methylphenyl]benzenesulfonamide

To 216 mg (0.734 mmol) of 2-[(4-(tert-butoxycarbonylamino)butoxy]4-methylaniline, as prepared in preceding step, and 101 μL (0.918 mmol) of 4-methylmorpholine in 3.0 mL of dichloromethane was added 143 μL (0.807 mmol) of benzenesulfonyl chloride. The solution was stirred for 45 min, diluted with 30 μL of dichloromethane and washed with 10% citric acid (2×30 μL), saturated NaHCO$_3$ (2×30 mL), and brine (30 mL). The solution was dried (Na$_2$SO$_4$) and concentrated to 342 mg of a faintly amber solid. Chromatography on a Waters Associates 10 g silica Sep-Pak SPE column eluting with a gradient of 0–4% ethyl acetate—dichloromethane afforded 282 mg (88%) of the title compound as a white crystalline solid. $^1$H-NMR (300 MHz, CDCl$_3$) δ 7.72 (m, 2 H), 7.50 (m, 1 H), 7.40 (m, 3 H), 6.94 (s, 1 H), 6.83 (dd, 1 H, J=8.3,2.1 Hz 6.59 (d, 1 H, J=8.3 Hz), 4.54 (br s, 1 H), 3.70 (t, 2 H, J=6.3 Hz), 3.19 (q, 2 H, J=6.5 Hz), 2.27 (s, 3 H), 1.62 (m, 2 H), 1.48 (m, 2 H), and 1.46 (s, 9 H). Mass spectrum (MALDI-TOF, gentisic acid matrix) calcd. for $C_{22}H_{30}N_2O_5S$: 457.2 (M+Na). Found: 457.7.

d) N-[2-(N,N-Dimethylamino)ethyl]-N-[2-[4-(tert-butoxycarbonylamino)-butoxy]-4-methylphenyl]benzenesulfonamide To a solution of 82.2 mg (0.189 mmol) of N-[2-[4-(tert-butoxycarbonylamino)butoxy]-4-methylphenyl]benzenesulfonamide, as prepared in preceding step, in 1.5 mL of anhydrous N,N-dimethylformamide was added 78.3 mg (0.567 mmol) of powdered anhydrous potassium carbonate and 30 mg (0.208 mmol) of N,N-dimethylaminoethyl chloride hydrochloride. After stirring at 50° C. for 21 h, the mixture was partitioned between 10 mL of ethyl acetate and 10 mL of water. The organic layer was washed with water (10 mL) and brine (10 mL), dried (Na$_2$SO$_4$) and concentrated to give 93.7 mg of a colorless oil. Chromatography on a 10 g Waters Associates Sep-Pak silica SPE column with 50% ethyl acetate—dichloromethane afforded a small amount of unreacted starting material (7.4 mg) followed by 10% methanol—dichloromethane afforded 67.2 mg (77% based on recovered starting material) of the title compound as a colorless resin. $^1$H-NMR (300 MHz, CDCl$_3$) δ 7.67 (m, 2 H), 7.53 (m, 1 H), 7.43 (m, 2 H), 7.11 (d, 1 H, J=2.0 Hz), 7.06 (dd, 1 H, J=8.4, 1.7 Hz), 6.66 (d, 1 H, J=8.4), 4.53 (br s, 1 H), 3.4–3.8 (br m, 4 H), 3.04 (q, 2 H, J=6.3 Hz), 2.88 (m, 2 H), 2.28 (s, 3 H), 2.22 (s, 6 H), 1.46 (s, 9 H), and 1.33 (m, 4 H). Mass spectrum (MALDI-TOF, α-cyano-4-hydroxycinnamic acid matrix) calcd. for $C_{26}H_{39}N_3O_5S$: 506.3 (M+H), 528.3 (M+Na). Found: 506.5, 528.8.

e) N-[2- (N,N-Dimethylamino)ethyl]-N-[2-[[4-(1-acetimidoyl) amino]butoxy]-4-methylphenyl]benzenesulfonamide Dihydrochloride To a solution of 82.0 mg (0.162 mmol) of N-[2-(N,N-dimethylamino) ethyl]-N-[2-[4-(tert-butoxycarbonylamino)butoxy]-4-methylphenyl]benzenesulfonamide, as prepared in preceding step, in 2.0 mL of anhydrous dichloromethane was added 2.0 mL of trifluoroacetic acid. After stirring for 15 min, the solution was concentrated and placed under vacuum (0.5 torr/1 h) to afford a colorless oil. This residue in 0.75 mL of anhydrous N,N-dimethylformamide was treated with 30.0 mg (0.243 mmol) of ethyl acetimidate hydrochloride and 127 μL (0.729 mmol) of N,N-diisopropylethylamine and the mixture stirred for 20 h at ambient temperature. 1 N NaOH (10 mL) was added and the mixture extracted with ethyl acetate (3×10 mL). The combined extracts were washed with 10 mL of brine-1 N NaOH (9:1), dried (Na$_2$SO$_4$) and concentrated to 88 mg of a pale yellow resin. The above residue in 1.0 mL of anhydrous dichloromethane was treated with 101 μL (0.405 mmol) of 4 M HCl in dioxane and the solution concentrated in vacuo to a pale yellow resin. Concentration four more times from 2.0 mL of dichloromethane and placement under vacuum (0.5 torr/3 h) afforded 77.0 mg (91%) of a hard off-white foam. Mass spectrum (MALDI-TOF, α-cyano-4-hydroxycinnamic acid matrix) calcd. for $C_{23}H_{34}N_4O_3S$: 447.2 (M+H). Found: 447.3.

EXAMPLE 4

N-Benzyl-N-[[[3-(1-acetimidoyl)piperidin-4-yl]methylamino]phenyl]benzene Sulfonamide a) N-(3-nitrophenyl)benzenesulfonamide To 6.17 g (44.7 mmol) of 3-nitroaniline and 8.41 mL (48.2 mmol) of N,N-diisopropylethylamine in 150 mL of anhydrous diethyl ether was added 5.14 mL (40.2 mmol) of benzenesulfonyl chloride. The mixture was heated to reflux under nitrogen with stirring for 16 h, cooled and the resulting two-phase mixture scratched to crystallize the insoluble oil. After decanting the ether layer, the derived solid was dissolved in 300 mL of dichloromethane and the solution washed with 2 N HCl (3×200 mL), saturated NaHCO$_3$ (200 mL), brine (200 mL), dried (Na$_2$SO$_4$) and concentrated to give 9.62 g (86%) of the title compound as a light tan solid. $^1$H-NMR (300 MHz, CDCl$_3$) δ 7.96 (m, 2 H), 7.86 (m, 2 H), 7.41–7.63 (m, 5 H), and 7.30 (br s, 1 H). Mass spectrum (MALDI-TOF, gentisic acid matrix)calcd. for C$_{12}$H$_{10}$N$_2$O$_4$S: 301.0 (M+Na). Found: 301.1.

b) N-Benzyl-N-(3-nitrophenyl)benzenesulfonamide

To 6.00 g (21.6 mmol) of N-(3-nitrophenyl) benzenesulfonamide, as prepared in preceding step, in 15 mL of anhydrous N,N-dimethylformamide under nitrogen was added 4.48 g (32.4 mmol) of powdered anhydrous potassium carbonate and 2.83 mL (23.8 mmol) of benzyl bromide. After stirring for 3.5 h, the mixture was partitioned between 200 mL of ethyl acetate and 250 mL of water. The aqueous layer was extracted with 50 mL of ethyl acetate and the combined organic phases washed with 1 M K$_2$CO$_3$ (2×100 mL). Hexane (50 mL) was added to the organic phase which was then washed with water (3×150 mL), brine (100 mL), dried (Na$_2$SO$_4$) and concentrated to give 8.2 g of a crystalline yellow solid. Recrystallization from ethyl acetate-hexane afforded 7.45 g (94%) of the title compound as cream-colored crystals. $^1$H-NMR (300 MHz, CDCl$_3$) δ 8.06 (d, 1 H, J=7.4 Hz), 7.76 (s, 1 H), 7.64–7.67 (m, 3 H), 7.51–7.56 (m, 2 H), 7.38–7.46 (m, 2 H ), 7.21 (s, 5 H), and 4.77 (s, 2 H). Mass spectrum (MALDI-TOF, gentisic acid matrix) calcd. for C$_{19}$H$_{16}$N$_2$O$_4$S: 369.1 (M+H), 391.1 (M+Na), 407.0 (M+K). Found: 368.8, 391.3, 407.4.

c) N-Benzyl-N-(3-aminophenyl)benzenesulfonamide

To 3.01 g (8.17 mmol) of N-benzyl-N-(3-nitrophenyl) benzenesulfonamide, as prepared in preceding step, in 60 mL of methanol-tetrahydrofuran (1:1) was added 200 mg of 10% palladium on carbon. After stirring the mixture under a balloon of hydrogen for 1.7 h, an additional 200 mg of 10% palladium on carbon was added and stirring was continued for another 2.5 h. Filtration (Celite) and concentration afforded a dark green resin which was dissolved in 40 mL of ethyl acetate-hexane (1:1), refiltered (Celite) and concentrated to afford 2.9 g of a yellow solid. Recrystallization from ethyl acetate-ether afforded 2.21 g (80%) of the title compound as a light orange crystalline powder. $^1$H-NMR (300 MHz, CDCl$_3$) δ 7.68–7.71 (m, 2 H), 7.56–7.62 (m, 1 H), 7.46–7.51 (m, 2 H), 7.18–7.2 (m, 5 H), 6.97 (t, 1 H, J=8.0 Hz), 6.58 (dd, 1 H, J=8.0, 1.6 Hz), 6.47 (t, 1 H, J=2.1 Hz), 6.32 (dd, 1 H, J=8.0, 1.3 Hz), and 4.70 (s, 1 H). Mass spectrum (MALDI-TOF, gentisic acid matrix) calcd. for C$_{19}$H$_{18}$N$_2$O$_2$S: 339.1 (M+H), 361.1 (M+Na). Found: 339.5, 361.5.

d) N-Benzyl-N-[[3-(N-tert-butoxycarbonylpiperidin-4-yl) carbonylamino]phenyl]benzenesulfonamide To 149 mg (0.650 mmol) of N-tert-butoxycarbonylisonipecotic acid, as prepared in step (a) in Example 1, and 287 mg (0.650 mmol) of Castro's Reagent (benzotriazole-1-yloxytris(dimethylamino)phosphonium hexafluorophosphate, BOP) in 1.5 mL of anhydrous N,N-dimethylformamide was added 155 μL (0.887 mmol) of N,N-diisopropylethylamine and the mixture stirred under nitrogen for 5 min. A solution of 200 mg (0.591 mmol) of N-benzyl-N-(3-aminophenyl) benzenesulfonamide, as prepared in preceding step, in 0.5 mL of N,N-dimethylformamide was added. After stirring for 16 h, 10 mL of saturated NaHCO$_3$ was added. The mixture was partitioned between 25 mL each of ethyl acetate and water. The organic layer was washed with 10% citric acid (2×20 mL), brine (20 mL) and dried (Na$_2$SO$_4$). Concentration afforded 360 mg of a yellow resin which was chromatographed on a Waters Associates 10 g silica Sep-Pak SPE column. Elution with a gradient of 5–10% ethyl acetate-dichloromethane afforded 268 mg (82%) of the title compound as a white foam. $^1$H-NMR (300 MHz, CDCl$_3$) δ 7.56–7.66 (m, 4 H), 7.47 (m, 2 H), 7.09–7.22 (m, 8 H), 6.60 (br d, 1 H, J=8.0 Hz), 4.70 (s, 2 H), 4.14 (br s, 2 H), 2.74 (br t,2H, J=12 Hz), 2.24–2.34 m, 1 H), 1.84 (br s, 1 H), 1.81 (br s, 1 H), 1.69 (td, 2 H, J=12.2, 4.1 Hz), and 1.44 (s, 9 H). Mass spectrum (MALDI-TOF, gentisic acid matrix) calcd. for C$_{30}$H$_{35}$N$_3$O$_5$S: 450.6 (M–BOC+2 H). Found: 450.3.

e) N-Benzyl-N-[[[3-(1-tert-butoxycarbonyl)piperidin-4-yl]methylamino]phenyl]benzenesulfonamide To 404 μL (0.807 mmol) of 2 M lithium borohydride in tetrahydrofuran was added 1.0 mL of tetrahydrofuran followed by 204 μL (1.61 mmol) of chlorotrimethylsilane. After stirring for 4 min, 148 mg (0.269 mmol) of N-benzyl-N-[[3-(1-tert-butoxycarbonyl)piperidin-4-ylcarbonylamino]phenyl]benzenesulfonamide, as prepared in preceding step, in 2.0 mL of tetrahydrofuran was added and the mixture heated at 50° C. under nitrogen for 2 h. After quenching the reaction with 0.16 mL of MeOH, 1.0 mL of 2 N NaOH was added, the mixture stirred for 10 min and then extracted with ethyl acetate (2×10 mL). The combined extracts were washed with brine, dried (Na$_2$SO$_4$) and concentrated to 150 mg of a pale yellow resin. Chromatography on a Waters Associates 10 g silica Sep-Pak SPE column eluting with 5% ethyl acetate—dichloromethane afforded 143 mg (99%) of the title compound as a colorless resin. $^1$H-NMR (300 MHz, CDCl$_3$) δ 7.70–7.74 (m, 2 H), 7.59 (m, 1 H), 7.48 (m, 2 H), 7.22 (m, 5 H), 6.95 (t, 1 H, J=8.0 Hz), 6.40 (dd, 1 H, J=8.1, 2.2 Hz), 6.25 (t, 1 H, J=2.1 Hz), 6.17 (dd, 1 H, J=7.2, 1.8 Hz), 4.70 (s, 2 H), 4.11 (br s, 2 H), 3.66 (br s, 1 H), 2.85 (br s, 2 H), 2.66 (t, 2 H, J=13.3 Hz), 1.65 (d, 2 H, J=13.3 Hz), 1.47 (s, 9 H), and 1.09 (m, 2 H). Mass spectrum (MALDI-TOF, gentisic acid matrix) calcd. for C$_{30}$H$_{37}$N$_3$O$_4$S: 435.6 (M–BOC+H). Found: 435.6.

f) N-Benzyl-N-[[[3-(1-acetimidoyl)piperidin-4-yl]methylamino]phenyl]benzenesulfonamide To 140 mg (0.261 mmol) of N-benzyl-N-[[[3-(1-tert-butoxycarbonyl) piperidin-4-yl]methylamino]phenyl] benzenesulfonamide, as prepared in preceding step, in 3.0 mL of anhydrous dichloromethane was added 0.75 mL of trifluoroacetic acid. After stirring for 15 min, the solution was concentrated and placed under vacuum (0.1 torr/1 h) to afford a colorless resin. This residue in 1.0 mL of anhydrous N,N-dimethylformamide was treated with 64.5 mg (0.522 mmol) of ethyl acetimidate hydrochloride and 182 μL (1.04 mmol) of N,N-diisopropylethylamine and the mixture stirred for 48 h. An additional 64.5 mg (0.522 mmol) of ethyl acetimidate hydrochloride and 91.0 μL (1.04 mmol) of N,N-diisopropylethylamine was added and the mixture stirred at 50° C. for 20 h. To the mixture was added 20 mL of ethyl acetate and the solution washed with 0.1 N NaOH (2×20 mL). The combined aqueous layers were extracted with ethyl acetate (4×10 mL) and the five combined organic layers washed with 25 mL of brine and dried (Na$_2$SO$_4$) and concentrated to 91.4 mg of a pale yellow resin. This material was crystallized obtaining three crops from methanol-ethyl acetate and two crops from methanol-ethyl acetate-diethyl ether to afford 54.8 mg (44%) of the title compound as a cream-colored powder. $^1$H-NMR (300 MHz, CD$_3$OD) δ 7.65–7.72 (m, 3 H), 7.54–7.58 (m, 2 H), 7.18–7.24 (m, 5 H), 6.90 (t, 1 H, J=8.1 Hz), 6.46 (dd, 1 H, J=8.2, 2.0 Hz), 6.25 (t, 1 H, J=2.1 Hz), 6.13 (d, 1 H, J=7.8 Hz), 4.73 (s, 2 H), 4.02 (m, 2 H), 3.05–3.25 (m, 2 H), 2.88 (d, 2 H, J=6.2 Hz), 2.31 (s, 3 H), 1.89 (m, 3 H), and 1.30 (m, 2 H). Mass spectrum (MALDI-TOF, α-cyano-4-hydroxycinnamic acid matrix) calcd. for C$_{27}$H$_{32}$N$_4$O$_2$S: 477.2 (M+H). Found: 477.2.

EXAMPLE 5

3-Chlorobenzenesulfonic Acid 3-[[(1-Acetimidoyl)piperidin-4-yl]methoxy]-5-methylphenyl Ester Hydrochloride a) 3-Chlorobenzenesulfonic Acid 3-hydroxy-5-methylphenyl Ester Orcinol monohydrate (1.42 g, 10 mmol) and 3-chlorobenzenesulfonyl chloride (2.43 g, 11 mmol) were mixed in saturated $NaHCO_3$ (30 mL) and diethyl ether (30 mL). The biphasic mixture was stirred vigorously at room temperature for 2 days. After adding water (50 mL) to the mixture, the mixture was extracted with ethyl acetate (3×50 mL). The organic phase was then washed with brine (2×50 mL) and dried over $Na_2SO_4$. The solvent was removed in vacuo and the residue was purified by flash column chromatography (2% ethyl acetate in methylene chloride) to give the title compound as a pale-yellow liquid (2.08 g, 69%). $^1$H-NMR (300 MHz, $CDCl_3$) δ 2.24 (s, 3 H), 5.32 (s, 1 H), 6.33 (t, 1 H, J=2.2 Hz), 6.40 (s, 1 H), 6.57 (s, 1 H), 7.48 (t, 1 H, J=8.0 Hz), 7.65 (m, 1 H), 7.73 (m, 1 H), and 7.86 (t, 1 H, J=1.8 Hz).

b) 3-Chlorobenzenesulfonic Acid 3-[[N-(tert-Butoxycarbonyl)piperidin4-yl]methoxy]-5-methylphenyl Ester Diethyl azodicarboxylate (349 mg, 2.0 mmol) was added to a solution of 3-chlorobenzenesulfonic acid 3-hydroxy-5-methylphenyl ester (600 mg, 2.0 mmol), as prepared in the preceding step, N-tert-butoxycarbonyl4-piperidinemethanol (430 mg, 2.0 mmol), as prepared in step (b) of Example 1, and triphenylphosphine (525 mg, 2.0 mmol) in tetrahydrofuran (20 mL) at 0° C. The mixture was stirred at 0° C. for 2 h and at room temperature for 3 h. The reaction was quenched with water (50 mL) and extracted with ethyl acetate (3×50 mL). The organic phase was washed with saturated $NaHCO_3$ (2×50 mL), brine (2×50 mL) and dried over $Na_2SO_4$. The solvent was removed in vacuo and the residue was purified by flash column chromatography (1:3 ethyl acetate/hexane) to give the title compound as a colorless liquid (800 mg, 81%). $^1$H-NMR (300 MHz, $CDCl_3$) δ 1.24 (m, 2 H), 1.47 (s, 9 H), 1.75 (m, 2 H). 1.90 (m, 1 H), 2.25 (s, 3 H), 2.73 (t, 2 H, J=12.5 Hz), 3.68 (d, 2 H, J=3.1 Hz), 4.13 (m, 2 H), 6.34 (t, $^1$H, J=2.2 Hz), 6.39 (s, 1 H), 6.61 (s, 1 H), 7.49 (t, 1 H, J=7.8 Hz), 7.63 (d, 1 H, J=0.7 Hz), 7.75 (d, 1 H, J=3.9 Hz), and 7.86 (t, 1 H, J=1.8 Hz).

c) 3-Chlorobenzenesulfonic Acid 3-[[(1-Acetimidoyl)piperidin-4-yl]methoxy]-5-methylphenyl Ester Hydrochloride 3-Chlorobenzenesulfonic acid 3-[[N-(tert-butoxycarbonyl)piperidin-4-yl]methoxy]-5-methylphenyl ester (496 mg, 1.0 mmol), as prepared in the preceding step, was stirred with 4 N HCl in 1,4-dioxane (15 mL) at room temperature for 2 h. The solvent was removed in vacuo, and the residue was co-evaporated with methylene chloride several times to give the amine hydrochoride salt. The amine hydrochloride salt was then treated with triethylamine (1.0 mL) and ethyl acetimidate hydrochloride (247 mg, 2.0 mmol) in N,N-dimethylformamide (10 mL) and stirred at room temperature overnight. The N,N-dimethylformamide was removed in vacuo. The residue was partitioned between methylene chloride (200 mL) and 10% $K_2CO_3$ (50 mL). The organic phase was washed with 10% $K_2CO_3$ (2×50 mL) and dried over $K_2CO_3$. The solvent was removed in vacuo, the residue treated with HCl-methanol (30 mL), and then concentrated in vacuo. The residue was then purified by chromatography (15% methanol in methylene chloride) and crystallized (methanol—ethyl acetate) to give the title compound as white crystals (275 mg, 58%). $^1$H-NMR (300 MHz, DMSO-$_6$) δ 1.34 (m, 2 H), 1.84 (d, 2 H, J=7 Hz), 2.06 (m, 1 H), 2.22 (s, 3 H), 2.28 (s, 3 H), 3.16 (m, 2 H), 3.78 (d, 2 H, J=3.1 Hz), 3.93 (d, 1 H, J=6.5 Hz), 4.12 (d, 1 H, J=6.5 Hz), 6.43 (t, 1 H, J=2.1 Hz), 6.49 (s, 1 H), 6.77 (s, 1 H), 7.72 (t, 1 H, J=7.5 Hz), 7.85 (t, 1 H, J=1.4 Hz,), 7.92 (m, 2 H), 8.67 (br s, 1 H), and 9.24 (br s, 1 H). Mass spectrum (MALDI-TOF, sinapinic acid matrix) calcd. for $C_{21}H_{25}N_2O_4SCl$: 437.1 (M+H). Found: 436.8.

EXAMPLE 6

2-Chlorobenzenesulfonic Acid 3-[(3-Amidinophenyl)methoxy]-5-methylphenyl Ester Hydrochloride a) 2-Chlorobenzenesulfonic Acid 3-[(3-Cyanophenyl)methoxy]-5-methylphenyl Ester Diethyl azodicarboxylate (349 mg, 2.0 mmol) was added to a solution of 2-chlorobenzenesulfonic acid 3-hydroxy-5-methylphenyl ester (900 mg, 3.0 mmol), as prepared in step (c) of Example 1, 3-cyanobenzyl alcohol (400 mg, 3.0 mmol; Yoon et al., J. Org. Chem. 38:2786–2792 (1973)), and triphenylphosphine (525 mg, 2.0 mmol) in tetrahydrofuran (20 mL) at 0° C. The mixture was stirred at 0° C. for 2 h and at room temperature for 3 h. The reaction mixture was quenched with water (50 mL) and extracted with ethyl acetate (3×50 mL). The organic phase was washed with saturated $NaHCO_3$ (2×50 mL), brine (2×50 mL) and dried over $Na_2SO_4$. The solvent was removed in vacuo and the residue was purified by flash column chromatography (2:1 ethyl acetate/hexane) to give the title compound as a white solid (1.10 g, 89%). $^1$H-NMR (300 MHz, $CDCl_3$) δ 2.26 (s, 3 H), 4.99 (s, 2 H), 6.55 (t, 1 H, J=2.3 Hz), 6.60 (t, 1 H, J=0.7 Hz), 6.67 (t, 1 H, J=0.7 Hz), 7.39 (m, 1 H), 7.50 (t, 1 H, J=7.7 Hz), 7.61 (m, 5 H), and 7.96 (d, 1 H, J=1.3 Hz).

b) 2-Chlorobenzenesulfonic Acid 3-[(3-Amidinophenyl)methoxy]-5-methyl-phenyl Ester Hydrochloride To a solution of 2-chlorobenzenesulfonic acid 3-[(3-cyanophenyl) methoxy]-5-methylphenyl ester (207 mg, 0.5 mmol), as prepared in the preceding step, in methylene chloride (10 mL) was added 37% HCl in ethanol (10 mL) at 0° C. The mixture was allowed to stand at 0° C. for 3 days. The solvent was evaporated in vacuo and the residue was co-evaporated with methylene chloride several times. The residue was dissolved in ethanol (10 mL) and ammonium carbonate (192 mg, 2.0 mmol) was added at 0° C. The mixture was stirred at room temperature overnight. Methylene chloride (150 mL) was added to the mixture. The methylene chloride solution was washed with 10% $K_2CO_3$ (2×50 mL) and dried over $K_2CO_3$. The solvent was removed in vacuo, HCl in methanol (30 mL) was added, and the solvent again removed in vacuo. The residue was purified by flash chromatography (10% methanol in methylene chloride) to give the title compound as a white solid (112 mg, 48%). $^1$H-NMR (300 MHz, DMSO-$d_6$) δ 2.23 (s, 3 H), 5.11 (s, 2 H), 6.54 (s, 1 H), 6.56 (s, 1 H), 6.88 (s, 1 H), 7.58 (t, 1 H, J=6.5 Hz), 7.61 (t, 1 H, J=12.2 Hz), 7.66 (d, 1 H, J=3.9 Hz), 7.73–7.95 (m, 5 H), and 9.40 (br s, 4 H). Mass spectrum (MALDI-TOF, sinapinic acid matrix) calcd. for $C_{21}H_{19}N_2O_4SCl$: 431.1 (M+H), 453.1 (M+Na). Found: 0 431.0, 452.9.

EXAMPLE 7

2-Chlorobenzenesulfonic Acid 3-[[3-(N-Hydroxy)amidinophenyl]methoxyl]-5-methylphenyl Ester Hydrochloride To a solution of 2-chlorobenzenesulfonic acid 3-[(3-cyanophenyl) methoxy]-5-methylphenyl ester (207 mg, 0.5 mmol), as prepared in step (a) of the Example 6, in methylene chloride (10 mL) was added 37% HCl in ethanol (10 mL) at 0° C. The mixture was allowed to stand at 0° C. for 3 days. The solvent was removed in vacuo and the residue was co-evaporated with methylene chloride several times. The residue was dissolved in ethanol (10 mL) and then treated with hydroxylamine hydrochloride (140 mg, 2.0 mmol) and $Na_2CO_3$ (106 mg, 1.0 mmol). The reaction mixture was stirred at room temperature for 2 days. Methylene chloride (150 mL) was added to the mixture, washed with 10% $K_2CO3$ (2×50 mL), and dried over $K_2CO_3$. The solvent was removed in vacuo, HCl in methanol (30 mL) added and the solvent removed in vacuo. The residue was purified by flash chromatography (1:1 ethyl acetate/methylene chloride) to give the title compound as a white foam (95 mg, 39%). $^1$H-NMR (300 MHz, $CDCl_3$) δ 2.25 (s, 3 H), 4.89 (br s, 1 H), 4.98 (d, 2 H, J=10.7 Hz), 5.58 (br s, 1 H), 6.15 (br s, 1 H), 7.33–7.64 (m, 6 H), 7.76–7.83 (m, 1 H), and 7.92 (d, 1 H, J=4.0 Hz). Mass spectrum (MALDI-TOF, sinapinic acid matrix) calcd. for $C_{21}H_{19}N_2O_5SCl$: 447.1 (M+H), 469.1 (M+Na). Found: 447.1, 469.2.

EXAMPLE 8

2,3-Dichlorobenzenesulfonic Acid 3-[[(1-Acetimidoyl)piperidin-4-yl]methoxy]-5-methylphenyl Ester Hydrochloride a) 2,3-Dichlorobenzenesulfonic Acid 3-hydroxy-5-methylphenyl ester A solution of orcinol monohydrate (0.7.1 g, 5.0 mmol) and 2,3-dichlorobenzenesulfonyl chloride (1.23 g, 5.0 mmol) in saturated $NaHCO_3$ (20 mL) and diethyl ether (20 mL was stirred at room temperature for 2 days. The reaction mixture was quenched with water (50 mL) and extracted with ethyl acetate (3×50 mL). The organic phase was washed with brine (2×50 mL) and dried over $Na_2SO_4$. The solvent was evaporated in vacuo and the residue was purified by flash column chromatography (methylene chloride to 2% ethyl acetate in methylene chloride) to give the title compound as a pale yellow oil (0.89 g, 55%). $^1$H-NMR (300 MHz, $CDCl_3$) δ 2.24 (s, 3 H), 5.23 (s, 1 H), 6.43 (t, 1 H, J×2.2 Hz), 6.54 (d, 2 H, J=1.1 Hz), 7.34 (t, 1 H, J=8.1 Hz), 7.75 (dd, 1 H, J=0.8, 4.0 Hz), and 7.91 (dd, 1 H, J=0.8, 4.0 Hz).

b) 2,3-Dichlorobenzenesulfonic Acid 3[[N-(tert-Butoxycarbonyl)piperidin-4-yl]methoxy]-5-methylphenyl Ester Diethyl azodicarboxylate (349 mg, 2.0 mmol) was added to a solution of 2,3-dichlorobenzenesulfonic acid 3-hydroxy-5-methylphenyl ester (644 mg, 2.0 mmol), as prepared in the preceding step, N-tert-butoxylcarbonyl-4-piperidinemethanol (430 mg, 2.0 mmol), as prepared in step (b) of Example 1, and triphenylphosphine (525 mg, 2.0 mmol) in tetrahydrofuran (20 nL) at 0° C. The mixture was stirred at 0° C. for 2 h and at room temperature for 3 h. The reaction mixture was quenched with water (50 mL) and extracted with ethyl acetate (3×50 mL). The organic phase was washed with saturated $NaHCO_3$ (2×50 mL), brine (2×50 mL) and dried over $Na_2SO_4$. The solvent was removed in vacuo and the residue was purified by flash column chromatography (1:3 ethyl acetate/hexane) to give the title compound as a colorless syrup (930 mg, 88%). $^1$H-NMR (300 MHz, $CDCl_3$) δ 1.26 (m, 2 H), 1.47 (s, 9 H), 1.75 (m, 2 H), 1.90 (m, 1 H), 2.25 (s, 3 H), 2.73 (t, 2 H, J=2.0 Hz), 3.68 (d, 2 H, J=3.2 Hz), 4.13 (m, 2 H), 6.47 (d, 1 H, J=1.1 Hz), 6.53 (d, 1 H, J=0.4 Hz), 6.59 (s, 1 H), 7.34 (t, 1 H, J=8.2 Hz), 7.75 (m, 1 H), and 7.92 (m, 1 H).

c) 2,3-Dichlorobenzenesulfonic Acid 3-[[(1-Acetimdoyl)piperidin-4-yl]methoxy]-5-methylphenyl Ester Hydrochloride 2,3-Dichlorobenzenesulfonic acid 3-[[N-(tert-butoxycarbonyl)piperidin-4-yl]methoxy]-5-methylphenyl ester (530 mg, 1.0 mmol), as prepared in the preceding step, was stirred with 4 N HCl in 1,4-dioxane (10 mL) at room temperature for 2 h. The solvent was evaporated in vacuo, the residue was co-evaporated with methylene chloride several times to give the amine HCl salt. Triethylamine (0.5 mL) and ethyl acetimidate hydrochloride (247 mg, 2.0 mmol) were added to a solution of the above amine in N,N-dimethylformamide (10 mL) and the reaction mixture was stirred at room temperature for 2 days. The N,N-dimethylformamide was removed in vacuo and the residue was partitioned between methylene chloride (200 mL) and 10% $K_2CO_3$ (50 mL). The organic phase was washed with 10% $K_2CO_3$ (2×50 mL) and dried over $K_2CO_3$. After removing the solvent in vacuo, HCl-methanol (30 mL) was added and the solution concentrated. The residue was then crystallized from methanol-ethyl acetate to give the title compound as white crystals (420 mg, 83%). $^1$H-NMR (300 MHz, DMSO-$d_6$) δ 1.34 (m, 2 H), 1.84 (d, 1 H, J=8.6 Hz), 2.04 (m, 1 H), 2.22 (s, 3 H), 2.29 (s, 3 H), 3.16 (m, 2 H), 3.78 (d, 2 H, J=3.2 Hz), 3.92 (d, 1 H, J=7.0 Hz), 4.15 (d, 1 H, J=7.0 Hz), 6.46 (t, 1 H, J=2.2 Hz), 6.52 (s, 1 H), 6.77 (s, 1 H), 7.62 (t, 1 H, J=8.1 Hz), 7.96 (d, 1 H, J=4.0 Hz), 8.14 (d, 1 H, J=4.0 Hz), 8.74 (br s, 1 H), and 9.32 (br s, 1 H). Mass spectrum (MALDI-TOF, sinapinic acid matrix) calcd. for $C_{21}H_{24}N_2O_4SCl_2$: 471.1 (M+H). Found: 471.1.

EXAMPLE 9

2-Chloro-N-[[3-[(1-acetimidoyl)piperidin-4-yl]methoxy]-5-trifluoromethylphenyl]benzenesulfonamide Hydrochloride a) 3-(Trifluoromethyl)-5-nitrophenol 3-Methoxy-5-nitrobenzotrifluoride (5 g, 23 mmol) was dissolved in anhydrous methylene chloride (100 mL) and cooled to −80° C. under a nitrogen atmosphere. To this solution was added via dropping funnel a 1 M solution of $BBr_3$ in methylene chloride (68 mL, 68 mmol). This solution was allowed to warm to room temperature and stirred for 3 days. Water was slowly added to the mixture and mixed well to quench the excess $BBr_3$. To this mixture ether (500 mL) was added. The organic layer was separated and extracted with 2 N NaOH (240 mL). The alkaline extract was neutralized with dilute HCl and extracted with diethyl ether (3×300 mL). The ether extracts were combined, washed with saturated NaCl and dried over anhydrous $MgSO_4$. Evaporation of diethyl ether gave a brownish yellow oil which was chromatographed on a silica column to give 1.6 g (34%) of a yellow solid. $^1$H-NMR ($CDCl_3$/$CD_3OD$; 300 MHz) δ 7.38–7,40 (m, 1 H), 7.82 (t, 1 H, J=2.2 Hz), and 7.95–7.96 (m, 1 H).

b) 3-[[1-(Tert-Butoxycarbonyl)piperidin-4-yl]methoxy]-5-nitrobenzotrifluoride

The title compound was synthesized by treating 3-(trifluoromethyl)-5-nitrophenol (1.47 g, 7.1 mmol), as prepared in the preceding step, in a manner analogous to step (d) of Example 1 to give 2.17 g (76%) as an oil. $^1$H-NMR ($CDCl_3$, 300 MHz) δ 1.24–1.38 (m, 2 H), 1.48 (s, 9 H), 1.82–1.87 (m, 2 H), 1.96–2.10 (m, 1 H), 2.73 –2.81 (m, 2 H), 3.93 (d, 2 H, J=6.3 Hz), 4.09–4.21 (m, 2 H), 7.45–7.46 (m, 1 H), 7.89 (t, 1 H, J=2.2 Hz), and 8.07–8.08 (m, 1 H).

c) 2-Chloro-N-[[3-[(1-tert-butoxycarbonyl)piperidin-4-yl]methoxy]-5-trifluoromethylphenyl]benzenesulfonamide To a methanolic solution of 3-[(piperidin-4-yl)methoxy]-5-nitrobenzotrifluoride (2.17 g in 200 mL), as prepared in the preceding step, and 10% Pd/C (300 mg) was stirred under a hydrogen atmosphere for 20 h. The catalyst was removed by filtration and the methanol was evaporated to give a white foam. The foam was dried under high vacuum overnight and dissolved in anhydrous methylene chloride (10 mL). The methylene chloride solution was cooled in an ice bath under a nitrogen atmosphere and 2-chlorobenzenesulfonyl chloride (1.17 g, 5.50 mmol) and N-methylmorpholine (6.05 mmol) were added and the mixture allowed to warm to room temperature. The mixture was stirred for 2 days at which time N-methylmorpholine (200 mL) was added and the mixture heated to reflux for 3 h. The methylene chloride solution was diluted with another 50 mL of methylene chloride and extracted with 10% citric acid and saturated NaHCO$_3$. The organic layer was separated, washed with saturated NaCl and dried over anhydrous MgSO$_4$. Evaporation of the methylene chloride gave an oil which was chromatographed on a silica column to give 2.4 g (80%) of a white solid. $^1$H-NMR (CDCl$_3$, 300 MHz) δ 1.17–1.31 (m, 2 H), 1.47 (s, 9 H), 1.75–1.80 (m, 2 H), 1.83–1.98 (m, 1 H), 2.69–2.78 (m, 2 H), 3.74 (d, 1 H, J=6.2 Hz), 4.09–4.16 (m, 2 H), 6.81 (b s, 1 H), 6.87–6.89 (m, 1 H), 6.90 (br s, 1 H), 7.34–7.43 (m, 2 H), 7.50–7.54 (m, 2 H), and 8.05–8.08 (m, 1 H).

d) 2-Chloro-N-[[3-[piperidin-4-yl]methoxy]-5-trifluoromethylphenyl]-benzenesulfonamide Trifluoroacetate 2-Chloro-N-[[3-[(1-tert-butoxycarbonyl)piperidin-4-yl]methoxy]-5-trifluoromethylphenyl]benzenesulfonamide (0.33 g, 0.64 mmol) was treated with 25% trifluoroacetic acid in methylene chloride (5 mL) at ambient temperature for 0.5 h. The reaction mixture was evaporated to dryness and azeotroped with acetonitrile (3 times). The residue was triturated with hexane (twice) and diethyl ether, then placed under high vacuum overnight. Mass spectrum (MALDI-TOF, gentisic acid matrix) calcd. for C$_{19}$H$_{20}$N$_2$O$_3$SClF$_3$: 449.1 (M+H). Found: 449.8.

e) 2-Chloro-N-[[3-[(1-acetimidoyl)piperidin-4-yl]methoxy]-5-trifluoromethylphenyl]benzenesulfonamide Hydrochloride 2-Chloro-N-[[3-[piperidin-4-yl]methoxy]-5-trifluoromethylphenyl]benzenesulfonamide trifluoroacetate from step (d) above was dissolved in N,N-dimethylformamide (10 mL) and treated with ethyl acetimidate hydrochloride (0.16 g, 1.28 mmol) and triethylamine (0.27 mL, 1.92 mmol). The reaction mixture was stirred at ambient temperature overnight. The reaction mixture was diluted with water (cloud point) to initiate crystallization. The solid precipitate was collected by filtration and washed with water. The solid was dried under high vacuum overnight to give 0.218 g of the title compound. $^1$H-NMR (DMSO-d$_6$, 300 MHz) δ 1.33 (m, 2 H), 1.84 (d, 3 H), 2.04–2.12 (m, 1 H), 2.26 (s, 3 H), 3.10–3.33 (m, 2 H), 3.74 (d, 2 H), 3.91–4.02 (m, 2 H), 6.32 (br s, 1 H), 6.57 (s, 1 H), 6.67 (br s, 1 H), 7.28–7.42 (m, 3 H), 7.93 (dd, 1 H), 8.48 (br s, 1 H), and 9.04 (br s, 1 H).

EXAMPLE 10

2-Chloro-N-(5-carboxypentyl)-N-[[3-[(1-acetimidoyl)piperidin-4-yl]methoxy]-5-trifluoromethylphenyl]benzenesulfonamide a) 2-Chloro-N-(5-ethoxycarbonylpentyl)-N-[[3-[(1-tert-butoxycarbonyl)piperidin-4-yl]methoxy]-5-trifluoromethylphenyl]benzenesulfonamide A solution of 2-chloro-N-[[3-[(1-tert-butoxycarbonyl) piperidin-4-yl]methoxy]-5-trifluoromethylphenyl] benzenesulfonamide (0.6 g, 1.1 mmol) in N,N-dimethylformamide (10 mL) was treated with potassium carbonate (0.15 g, 1.1 mmol) and ethyl 6-bromohexanoate (0.20 mL, 1.1 mmol). The reaction was warmed at 50–60° C. for 2 days. The reaction mixture was diluted with water, neutralized with 5% hydrochloric acid, and extracted with ethyl acetate (3×). The ethyl acetate was washed with brine, dried (Na$_2$SO$_4$), and evaporated to dryness. The residue was purified by solid phase extraction using a 10 g Sep-Pak column (Waters Associates) and elution with 20% ethyl acetate—hexanes to give 0.70 g (92% yield). $^1$H-NMR (CDCl$_3$, 300 MHz) δ 1.26–1.43 (m, 2H), 1.44 (s, 9 H), 1.45–1.96 (m, 9 H), 2.24 (t, 2 H), 2.72 (br t, 2 H), 3.73–3.81 (m, 4 H), 4.05–4.16 (m, 4 H), 6.89 (br s, 1 H), 6.96 (m, 2 H), 7.24 (dt, 1 H), 7.40–7.50 (m, 2 H), and 7.81 (dd, 1 H).

b) 2-Chloro-N-(5-carboxypentyl)-N-[[3-[(1-tert-butoxycarbonyl)piperidin-4-yl]methoxy]-5-trifluoromethylphenyl]benzenesulfonamide A solution of 2-chloro-N-(5-ethoxycarbonylpentyl)-N-[[3-[(1-tert-butoxycarbonyl)piperidin-4-yl]methoxy]-5-trifluoromethylphenyl]benzenesulfonamide, as prepared in the preceding step, (0.70 g, 1 mmol) was dissolved in a 4:1 dioxane/water mixture (12 mL) and treated with lithium hydroxide monohydrate (0.042 g, 1 mmol). The reaction mixture was allowed to stir at ambient temperature for 2 days, then warmed at 50° C. overnight. An additional 0.042 g of lithium hydroxide monohydrate was added and the temperature maintained at 50° C. for 5 h. The reaction mixture was extracted with methylene chloride. The aqueous layer was acidified with 5% hydrochloric acid and extracted with methylene chloride. The combined methylene chloride extracts were washed with brine, dried (Na$_2$SO$_4$), and evaporated to dryness to give 0.68 g (quantitative) of the title compound. $^1$H-NMR (CDCl$_3$, 300 MHz) δ 1.20–2.00 (m, 20 H), 2.32 (t, 2 H), 2.75 (br t, 2 H), 3.76–3.84 (m, 4 H), 4.16 (m, 2 H), 6.92 (br s, 1 H), 6.99 (m, 2 H), 7.28 (dt, 1 H), 7.44 (dd, 1 H), 7.49 (dd, 1 H), and 7.84 (dd, 1 H).

c) 2-Chloro-N-(5-carboxypentyl)-N-[[3-[(1-acetimidoyl) piperidin-4-yl]methoxy]-5-trifluoromethylphenyl] benzenesulfonamide A solution of 2-chloro-N-(5-carboxypentyl)-N-[[3-[(1-tert-butoxycarbonyl)piperidin-4-yl]methoxy]-5-trifluoromethylphenyl]benzenesulfonamide, as prepared in the preceding step, (0.68 g, 1 mmol) in 25% trifluoroacetic acid in methylene chloride (15 mL) was stirred at ambient temperature for 0.5 h. The reaction mixture was evaporated to dryness, azeotroped with acetonitrile (3 times), and triturated with hexanes (twice) and 2:1 hexanes/diethyl ether (twice). The residue was placed under high vacuum to give 0.6 g of 2-chloro-N-(5-carboxypentyl)-N-[[3-[piperidin-4-yl]methoxy]-5-trifluoromethylphenyl]benzenesulfonamide trifluoroacetate.

A solution of 2-chloro-N-(5-carboxypentyl)-N-[[3-[piperidin-4-yl]methoxy]-5-trifluoromethylphenyl] benzenesulfonamide trifluoroacetate (0.3 g, 0.5 mmol) in N,N-diethylformamide (10 mL) was treated with triethylamine (0.21 mL, 1.5 mmol) and ethyl acetimidate hydrochloride (0.13 g, 1 mmol) at ambient temperature. The reaction mixture was diluted with water to produce an oily gum. The aqueous layer was decanted and the oily gum was treated with a small amount of methanol and diluted with water to initiate crystallization. The solid was collected by filtration, washed with water, and dried under high vacuum to give 7.4 mg of the title compounds as a white solid. $^1$H-NMR (CDCl$_3$/TFA, 300 MHz) δ 1.26–2.44 (m, 16 H), 2.9–3.4 (m, 2 H), 3.62–4.55 (m, 6 H), 6.90 (d, 1 H), 7.04–7.08 (m, 2 H), 7.33 (dt, 1 H), 7.55 (m, 2 H), and 7.84 (d, 1 H). Mass spectrum (MALDI-TOF, α-cyano-4- hydroxycinnamic acid matrix) calcd. for $C_{27}H_{33}N_3O_5SClF_3$: 604.2 (M+H). Found: 604.3.

EXAMPLE 11

1-(5-(N,N-Dimethylamino)naphthalenesulfonic Acid 3-[[(1-acetimidoyl)piperidin-3-yl]methoxy]-5-methoxyphenyl Ester Hydrochloride a) 1-(5-(N,N-Dimethylamino)naphthalenesulfonic Acid 3-Hydroxy-5-methoxyphenyl Ester A biphasic solution of 1.08 g (7.78 mmol) of 5-methoxyresorcinol, 2.10 g (7.78 mmol) of dansyl chloride, 30 mL of diethyl ether, and 30 mL of saturated sodium bicarbonate was vigorously stirred at ambient temperature overnight. The reaction mixture was quenched with pH 7 buffer, extracted into diethyl ether, dried ($MgSO_4$), and purified by flash chromatography (1–2% ether/methylene chloride) to provide 605.5 mg (21% yield) of the title compound was a bright yellow powder. $^1$H-NMR (300 MHz, $CDCl_3$) δ 8.59 (d, 1 H, J=8.5 Hz), 8.43 (d, 1 H, J=8 Hz), 8.12 (dd, 1 H, J=1, 7 Hz), 7.66 (dd, 1 H, J=8, 8.5 hz), 7.46 (dd, 1 H, J=7.4, 8.5 Hz), 7.25 (d, 1 H, J=7.5 Hz), 6.20 (t, 1 H, J=2.2 Hz), 6.04 (t, J=2.2 Hz), 6.01 (t, 1 H, J=2.2 Hz), 5.62 (br s, 1 H), 3.55 (s, 3 H), and 2.99 (s, 6 H). Mass spectrum (MALDI-TOF; α-cyano-4-hydroxycinnamic acid matrix) calcd. for $C_{19}H_{19}NO_5S$: 374.1 (M+H), 396.1 (M+Na). Found: 373.7, 395.7.

b) N-(tert-Butoxycarbonyl)-3-piperidinemethanol

To a solution of 3-piperidinemethanol (4.60 g, 40 mmol) and triethylamine (6 mL) in 1,4-dioxane (100 mL) was added slowly di-tert-butyl dicarbonate (8.72 g, 40 mmol). After stirring at room temperature for 2 h, the solvent was removed in vacuo and the residue purified by flash column chromatography (2:1 hexane/ethyl acetate) to give the title compound as white solid (7.81 g, 91%). $^1$H-NMR (300 MHz, $CDCl_3$) δ 1.25–1.39 (m, 2 H), 1.46 (s, 9 H), 1.60–1.81 (m, 3 H), 1.94 (br s, 1 H), 2.98–3.08 (m, 2 H), 3.51 (d, 2 H), and 3.66–3.77 (m, 2 H).

c) 1-(5-(N,N-Dimethylamino)naphthalenesulfonic Acid 3-[[N-(tert-Butoxycarbonyl)piperidin-3-yl]methoxy]-5-methoxyphenyl Ester To a solution of 379 mg (1.05 mmol) of 1-(5-(N,N-dimethylamino) naphthalenesulfonic acid 3-hydroxy-5-methoxyphenyl ester as prepared in Step a of this Example, in tetrahydrofuran (10 mL) containing 275 mg (0.347 mmol) of N-(tert-butoxycarbonyl)-3-piperidinemethanol, as prepared in the preceding step, 358 mg (1.36 mmol) of triphenylphosphine, and 350 μL (3.18 mmol) of N-methylmorpholine was added 215 μL (1.36 mmol) of diethyl azodicarboxylate. The reaction mixture was stirred at ambient temperature for 1 h, quenched with pH 7 buffer, extracted into diethyl ether, dried ($MgSO_4$), and concentrated in vacuo. The product was purified by flash chromatography to provide 245.7 mg (38% yield) of the title compound as a yellow foam. $^1$H-NMR (300 MHz, $CDCl_3$) δ 8.60 (d, 1 H, J=8.6 Hz), 8.45 (d, 1 H, J=8.7 Hz), 8.13 (dd, 1 H, J=1.2, 7.3 Hz), 7.67 (dd, 1 H), 7.47 (dd, 1 H, J=7.4, 8.5 Hz), 7.24 (1 H, J=8.5 Hz), 6.24 (t, 1 H, J=2.2 Hz), 6.10 (t, 1 H, J=1.9 Hz), 5.99 (t, 1 H, J=2.1 Hz), 3.88 (br d, 2 H), 3.55 (s, 3 H), 2.90 (s, 6 H), 1.58 (s, 3 H), and 1.44 (s, 9 H). Mass spectrum (MALDI-TOF; α-cyano-4-hydroxycinnamic acid matrix) calcd. for $C_{39}H_{38}N_2O_7S$: 593.2 (M+Na). Found: 593.0.

d) 1-(5-(N,N-Dimethylamino)naphthalenesulfonic Acid 3-[(piperidin-3-yl)methoxy]-5-methoxyphenyl Ester Hydrochloride To 245 mg of 1-(5-(N,N-dimethylamino) naphthalenesulfonic acid 3-[[N-(tert-butoxycarbonyl) piperidin-3-yl]methoxy]-5-methoxyphenyl ester, as prepared in the preceding step, in methylene chloride (1 mL) was added 500 μL of 4 N HCl in dioxane. The reaction mixture was stirred for 1 h. The reaction mixture was treated with another 1 mL of 4 N HCl in dioxane and stirring was continued for another 1 h. The reaction mixture was concentrated repeatedly from diethyl ether/methanol/hexane to afford 237.7 mg of the title compound as a hardened foam. $^1$H-NMR (300 MHz, DMSO-$d_4$) δ 9.19 (d, 1 H), 9.03 (q, 1 H), 8.72 (d, 1 H, J=8.5 Hz), 8.35 (d, 1 H, J=8.6 Hz), 8.17 (dd, 1 H, J=1.1, 7.3 Hz), 7.84 (t, 1 H, J=7.9 Hz), 7.69 (dd, 1 H, J=7.6, 8.5 Hz), 7.51 (1, H, J=7.7 Hz), 6.41 (t, 1 H, J=2.2 Hz), 6.08 (t, 1 H, J=2.1 Hz), 5.92 (t, 1 H, J=2.1 Hz), 3.57–3.76 (m, 2 H), 3.53 (s, 3 H), 3.2–3.23 (m, 2 H), 2.94 (s, 6 H), 2.58–2.8 (m, 2 H), 2.14 (br s, 1 H), 1.62–1.80 (m, 2 H), 1.17–1.3 (m, 1 H). Mass spectrum (MALDI-TOF; α-cyano-4-hydroxycinnamic acid matrix) calcd. for $C_5H_{30}N_2O_5S$: 471.2 (M+H), 493.2 (M+Na). Found: 470.9, 492.9.

e) 1-(5-(N,N-Dimethylamino)naphthalenesulfonic Acid 3-[[-1-Acetimidoyl)piperidin-3-yl]methoxy]-5-methoxyphenyl Ester Hydrochloride To a solution of 204.7 mg of 1-(5-(N,N-dimethylamino) naphthalenesulfonic acid 3-[(piperidin-3-yl)methoxy]-5-methoxyphenyl ester hydrochloride, as prepared in the preceding step in 2 mL of N,N-dimethylformamide containing 380 μL (3.42 mmol) of N,N-diisopropylethylamine was added 190 mg (1.54 mmol) of ethyl acetimidate hydrochloride. The reaction mixture was stirred at ambient temperature for 2 days. The solvent was removed in vacuo and the residue was quenched with 2 N sodium hydroxide. The reaction mixture was extracted into methylene chloride, dried ($K_2CO_3$), and concentrated in vacuo. The residue was dissolved in methylene chloride (1 mL), treated with 500 μL of glacial acetic acid and then flash chromatographed (methylene chloride/methanol/glacial acetic acid (92.6:6.5:0.9) to afford the acetic acid salt of the product as a gum. The gum was dissolved in methylene chloride and treated with 1 N sodium hydroxide. The organic phase was dried ($K_2CO_3$) and concentrated in vacuo. The residue was dissolved in methylene chloride, treated with 1 mL of 4 N HCl in dioxane and repeatedly concentrated from diethyl ether/methylene chloride/hexane to give 177 mg of the title compound as a pale yellow powder. $^1$H-NMR (300 MHz, DMSO-$d_6$) δ 9.37 and 9.33 (br s, 1 H), 8.78 (s, 1 H), 8.71 (d, 1 H, J=7.8 Hz), 8.34 (d, 1 H, J=8.6 Hz), 8.14–8.18 (m, 2 H), 7.84 (t, 1 H, J=7.8 Hz), 7.69 (dt, 1 H, J=1.1, 8.8 Hz), 7.49 (d, 1 H, J=7.6 Hz), 6.45 and 6.42 (t, 1 H), 6.16 and 6.10 (t, 1 H), 5.92 and 5.89 (t, 1 H), 3.53 (s, 3 H), 2.92 (t, 6 H), 2.28 and 2.22 (s, 3 H). Mass spectrum (MALDI-TOF; α-cyano-4-hydroxycinnamic acid matrix) calcd. for $C_{27}H_{33}N_3O_5S$: 512.2 (M+H). Found: 511.5.

EXAMPLE 12

2-Chlorobenzenesulfonic Acid 1-[[(1-Acetimidoyl) piperidin-4-yl]methoxy]naphthalen-3-yl Ester Acetic Acid Salt a) 2-Chlorobenzenesulfonic Acid 1-Hydroxynaphthalen-3-yl Ester At 0° C. to 1.0 g (6.24 mmol) of 1,3-naphthalenediol in tetrahydrofuran (20 mL) containing 1.5 mL of 2,6-lutidine was added 1.35 g (6.40 mmol) of 2-chlorobenzenesulfonyl chloride. The reaction mixture was stirred to ambient temperature overnight, quenched with 3 N hydrochloric acid, extracted into methylene chloride, and dried ($MgSO_4$). Purification by flash chromatography (2% ethyl acetate/methylene chloride) gave 277 mg (13% yield) of the title compound as a colorless solid. $^1$H-NMR (300 MHz, DMSO-d$_6$) δ 10.75 (s, 1 H), 8.06 (d, 1 H, J=1.7 Hz), 7.78–7.95 (m, 4 H), 7.43–7.57 (m, 3 H), 7.11 (d, 1 H, J=2 Hz), and 6.63 (d, 1 H, J=2 Hz).

b) 2-Chlorobenzenesulfonic Acid 1-[[1-N-(Tert-Butoxycarbonyl)piperidin-4-yl]methoxy]naphthalen-3-yl Ester To 277 mg (0.881 mmol) of 2-chlorobenzenesulfonic acid 1-hydroxynaphthalen-3-yl ester, as prepared in the preceding step, 180 mg (0.837 mmol) of N-tert-butoxycarbonyl-4-piperidinemethanol, as prepared in step (b) of Example 1, 260 mg ((0.99 mmol) of triphenylphosphine, and 270 μL (2.45 mmol) of N-methylmorpholine in 2 mL of tetrahydrofuran, was added 160 μL (1.02 mmol) of diethyl azodicarboxylate. The reaction mixture was stirred at ambient temperature for 1 h. The reaction mixture was quenched with water, extracted into diethyl ether, dried (MgSO$_4$), and flash chromatographed (2% diethyl ether/methylene chloride) to give 325 mg (79% yield) of a colorless foam. $^1$H-NMR (300 MHz, CDCl$_3$) δ 8.17 (d, 1 H, J=7 Hz), 7.96 (dd, 1 H, J=1.4, 8 Hz), 7.41–7.67 (m, 5 H), 7.34 (dt, 1 H, J=1, 7 Hz), 7.08 (d, 1 H), 6.64 (d, 1 H), J=2 Hz), 4.18 (br, 2 H), 3.89 (d, 2 H, J=6.2 Hz), 2.79 (t, 2 H, J=12H), 2.0–2.2 (m, 1 H), 1.76 (d, 2 H, J=8 Hz), and 1.49 (s, 9 H). Mass spectrum (MALDI-TOF; α-cyano-4-hydroxycinnamic acid matrix) calcd. for C$_{27}$H$_{30}$ClNO$_6$S: 554.1 (M+Na). Found: 554.2.

c) 2-Chlorobenzenesulfonic Acid 1-[(Piperidin-4-yl)methoxy]naphthalen-3-yl Ester Hydrochloride To a solution of 319 mg (0.596 mmol) of 2-chlorobenzenesulfonic acid 1-[[1-N-(tert-butoxycarbonyl)piperidin-4-yl]methoxy]naphthalen-3-yl ester, as prepared in the preceding step, in 2 mL of methylene chloride was added 1.5 mL (6 mmol) of 4 N HCl in dioxane. The reaction mixture was stirred for 1 h and triturated with diethyl ether to afford 281 mg of the title compound as a colorless powder. $^1$H-NMR (300 MHz, DMSO-d$_6$) δ 8.94 (bd, 1 H, J=9 Hz), 8.68 (bd, 1 H, J=10 Hz), 8.6 (d, 1 H, J=8 Hz), 7.8–7.98 (m, 4 Hz), 7.50–7.6 (m, 3 H), 7.18 (d, 1 H, J=2 Hz), 6.69 (d, 1 H, J=2 H), 3.94 (d, 2 H, J=7 Hz), 2.93 (q, 2 H), 2.16 (bm, 1 H), 1.96 (d, 2 H), and 1.57–1.71 (m, 2 H). Mass spectrum (MALDI-TOF; gentisic acid matrix) calcd. for C$_{22}$H$_{22}$ClNO$_4$S: 432.1 (M+H). Found: 431.5.

d) 2-Chlorobenzenesulfonic Acid 1-[[(1-Acetimidoyl)piperidin-4-yl]methoxy]naphthalen-3-yl Ester Acetic Acid Salt A mixture of 100 mg (0.214 mmol) of 2-chlorobenzenesulfonic acid 1-[(piperidin-4-yl)methoxy]naphthalen-3-yl ester hydrochloride, as prepared in the preceding step, in N,N-dimethylformamide (2 mL) containing 55 mg (0.45 mmol) of ethyl acetimidate hydrochloride and 125 μL of N,N-diisopropylethylamine was stirred at ambient temperature overnight. To the reaction mixture was added another 125 μL of N,N-diisopropylethylamine and 55 mg (0.45 mmol) of ethyl acetimidate hydrochloride. The reaction mixture was stirred for another 4 h. The reaction mixture was concentrated to dryness, quenched with 1 N sodium hydroxide (2 mL), extracted into methylene chloride, dried (K$_2$CO$_3$), and concentrated in vacuo. The residue was diluted with methylene chloride (1 mL), treated with 1 mL of glacial acetic acid and directly purified by preparative thin layer chromatography using methylene chloride/methanol/glacial acetic acid (93.6:6.5:0.5) as developing solvent to give the title compound. $^1$H-NMR (300 MHz, DMSO-d$_6$) δ 8.14 (d, 1 H, J=8 Hz), 7.8–7.97 (m, 4 H), 7.50–7.59 (m, 3 H), 7.19 (s, 1 H), 6.68 (d, 1 H, J=2 Hz), 4.11 (d, 2 H, J=6 Hz), 3.92 (d, 2 H, J=6Hz), 3.11 (t, 2 H, J=2.6 Hz), 2.2 (m, 1 H), 1.92 (d, 2 H), 1.75 (br s, 3 H), and 1.41 (q, 2 H). Mass spectrum (MALDI-TOF; α-cyano4-hydroxycinnamic acid matrix) calcd. for C$_{23}$H$_{24}$ClN$_3$O$_4$S: 474.1 (M+H). Found: 473.8.

EXAMPLE 13

3-[(2-Chlorophenoxy)methyl]-[[(1-acetimidoyl)piperidin-4-yl]methoxy]benzene acetic Acid Salt a) 3-[(2-Chlorophenoxy)methyl]phenol At 0° C. to 616 mg (2.35 mmol) of triphenylphosphine and 400 μL (3.84 mmol) of 2-chlorophenol in 20 niL of methylene chloride was added 370 mL (2.35 mmol) of diethyl azodicarboxylate followed by dropwise addition of a solution of 233 mg (1.9 mmol) 3-hydroxybenzyl alcohol in 2 mL of tetrahydrofuran. The reaction mixture was stirred at 0° C. to ambient temperature for 1 h. The reaction mixture was quenched with water, extracted into diethyl ether, dried (MgSO$_4$), and purified by flash chromatography (methylene chloride/hexane (2:1 to 4:1)) to provided 227 mg (44% yield) of the title compound as a colorless oil. $^1$H-NMR (300 MHz, CDCl$_3$) δ 7.39 (dd, 1 H, J=1.6, 7.8 Hz), 7.25 (t, 1 H), 7.15–7.21 (m, 1 H), 6.88–7.01 (m, 4 H), 6.79 (dd, 1 H, J=2.5, 8.1 Hz), 5.12 (s, 2 H), and 4.97 (s, 1 H).

b) 1-[(2-Chlorophenoxy)methyl]-3-[[N-(tert-butoxycarbonyl)piperidin-4-yl]methoxy]benzene To a solution of 272 mg (0.809 mmol) of 3-[(2-chlorophenoxy)methyl]phenol, as prepared in the preceding step, in methylene chloride (5 mL) containing 275 mg (1.05 mmol) of triphenylphosphine and 208 mg (0.97 mmol) of N-(tert-butoxycarbonyl)-4-piperidinemethanol, as prepared in step (b) of Example 1, was added slowly 165 μL (1.04 mmol) of diethyl azodicarboxylate. The reaction mixture was stirred at ambient temperature for 1 h. The reaction mixture was quenched with water, extracted into diethyl ether, dried (MgSO$_4$), and flash chromatographed (hexane/ethyl acetate (1:4 to 1:2)) to give 221 mg (58% yield) of the title compound as a colorless oil. $^1$H-NMR (300 MHz, CDCl$_3$) δ 7.38 (dd, 1 H, J=1.5, 7.8 Hz), 7.28 (t, 1 H, J=8.1 Hz), 7.15–7.21 (m, 1 H), 8.82–7.03 (m, 5 H), 5.13 (s, 2 H), 3.82 (d, 2 H, J=6.4 Hz), 2.74 (t, 2 H), 1.91–2.00 (m, 1 H), 1.84 (d, 2 H), and 1.47 (s, 9 H). Mass spectrum (MALDI-TOF; α-cyano-4-hydroxycinnamic acid matrix) calcd. for C$_{24}$H$_{30}$ClNO$_4$S: 454.2 (M+Na). Found: 454.4.

c) 1-[(2-Chlorophenoxy)methyl]-3-[(piperidin-4-yl)methoxy]benzene Hydrochloride

A solution of 215 mg of 1-[(2-chlorophenoxy)methyl]-3-[[N-(tert-butoxycarbonyl)piperidin-4-yl]methoxy]benzene, as prepared in the preceding step, in methylene chloride (2 mL) was treated with 1.5 mL of 4 N HCl in dioxane. The reaction mixture was stirred at ambient temperature for 1 h, and then concentrated to provide 183 mg of the title compound as a colorless powder after repeated concentrations from diethyl ether/hexane/methanol. $^1$H-NMR (300 MHz, DMSO-d$_6$) δ 8.51 (br s, 2 H), 7.45 (dd, 1 H, J=1.3, 7.9 Hz), 7.27–7.35 (m, 2 H), 7.21 (d, 1 H), 6.90–7.05 (m, 4 H), 5.18 (s, 2 H), 3.87 (d, 2 H), 2.90 (t, 2 H, J=10 Hz), 2.05 (m, 1 H), 1.91 (d, 2 H, J=13.8 Hz), and 1.5–1.54 (m, 2 H). Mass spectrum (MALDI-TOF; α-cyano-4-hydroxycinnamic acid matrix) calcd. for C$_{19}$H$_{22}$ClNO$_2$: 332.1 (M+H). Found: 332.0.

d) 3-[(2-Chlorophenoxy)methyl]-[[(1-acetimidoyl)piperidin-4-yl]methoxy]benzene Acetic Acid Salt To 40 mg (0.109 mmol) of 1-[(2-chlorophenoxy)methyl-]-3-[(piperidin-4-yl)methoxy]benzene hydrochloride as prepared in the preceding step, in 1 mL of N,N-dimethylformamide containing 100 μL (0.908 mmol) of N,N-diisopropylethylamine was added 40 mg (0.325 mmol) of ethyl acetimidate hydrochloride. The reaction mixture was stirred at ambient temperature for 3 days. The reaction mixture was concentrated in vacuo and the residue was quenched with 1 N sodium hydroxide, extracted into methylene choride, dried ($K_2CO_3$), and concentrated. The residue was dissolved with 1 mL of methylene chloride and then treated with 500 µL of glacial acetic acid. The solution was then applied directly to preparative thin layer chromatography using methylene chloride/methanol/glacial acetic (83:15:2) as developing solvent to provide 33.8 mg of the title compound as a gum. $^1$H-NMR (300 MHz, DMSO-$d_6$) δ 7.45 (dd, 1 H, J=1.5, 7.9 Hz), 7.27–7.34 (m, 2 H), 7.20–7.23 (dd, 1 H, J=1.4, 8.3 Hz), 6.89–7.04 (m, 4 H), 5.76 (s, 2 H), 4.07 (d, 2 H, J=14 Hz), 3.87 (d, 2 H, J=6.2 Hz), 3.05 (t, 2 H, J=13 Hz), 2.22 (s, 3 H), 2.05–2.13 (m, 1 H), 1.85 (d, 2 H), 1.71 (br s, 3 H), and 1.18–1.38 (m, 2 H). Mass spectrum (MALDI-TOF; α-cyano-4-hydroxycinnamic acid matrix matrix) calcd. for $C_{21}H_{25}N_2O_2$: 373.2 (M+H). Found: 373.0.

EXAMPLE 14

2-Chlorobenzenesulfonic Acid 3-[3-Amidinopropoxy]-5-methylphenyl Ester Hydrochloride a) 2-Chlorobenzenesulfonic Acid 3-[3-Cyanopropoxy]-5-methylphenyl Ester At 0° C. to 250 mg (0.796 mmol) of 2-chlorobenzenesulfonic acid 3-hydroxy-5-methylphenyl ester, as prepared in step (c) of Example 1 in N,N-dimethylformamide (3 mL) was added 20 mg (0.833 mmol) of 100% sodium hydride. The reaction mixture was stirred for 5 min. To the reaction mixture was added 100 µL (1.01 mmol) of 4-bromobutyronitrile. The reaction mixture was stirred to ambient temperature overnight, quenched with 1 N hydrochloric acid and extracted into diethyl ether. The reaction mixture was dried ($MgSO_4$), placed on a silica gel flash column, and eluted with methylene chloride to give 127 mg of impure compound as an oil, which was used as is in the next reaction. $^1$H-NMR (300 MHz, DMSO-$d_6$) δ 7.94 (dd, 1 H, J=1.5, 9 Hz), 7.54–7.63 (m, 2 H), 7.34–7.40 (m, 1 H), 6.57 (m, 1 H), 6.55 (m, 1 H), and 6.48 (t, 1 H, J=2 Hz). Mass spectrum (MALDI-TOF; α-cyano-4-hydroxycinnamic acid matrix) calcd. for $C_{17}H_{16}ClNO_4S$: 388.0 (M+Na). Found: 387.8.

b) 2-Chlorobenzenesulfonic Acid 3-[3-Amidinopropoxy]-5-methylphenyl Ester Hydrochloride A solution of 115 mg of 2-chlorobenzenesulfonic acid 3-[3-cyanopropoxy]-5-methylphenyl ester in 10 mL of 37% HCl in ethanol was stirred at 0° C. overnight. The reaction was concentrated to dryness, diluted with ethanol (5 mL) and treated with 1 g of ammonium carbonate. The reaction mixture was stirred for 40 min. The reaction mixture was quenched with 2 N sodium hydroxide, extracted into methylene chloride, dried ($K_2CO_3$), and concentrated to dryness. The residue was triturated with a mixture of methylene chloride/methanol/hexane to give 64 mg of the title compound as a colorless powder. $^1$H-NMR (300 MHz, DMSO-$d_6$) δ 9.02 (br s, 2 H), 8.68 (br s, 2 H), 7.95 (dd, 1 H, J=1, 7 Hz), 7.81–7.90 (m, 2 H), 7.56–7.62 (m, 1 H), 6.75 (s, 1 H), 6.50 (s, 1 H), 6.44 (t, 1 H, J=1 Hz), 3.89 (t, 2 H, J=6 Hz), 2.21 (s, 2 H), and 2.02 (pentet, 2 H). Mass Spectrum (MALDI-TOF; α-cyano-4-hydroxycinnamic acid matrix) calcd. for $C_{17}H_{19}ClN_2O_4S$: 383.1 (M+H). Found: 382.8.

EXAMPLE 15

2-Chlorobenzenesulfonic Acid 3-[[3-(N-Methyl)amidino)phenyl]methoxy]-5-methylphenyl Ester Hydrochloride To a solution of 2-chlorobenzenesulfonic acid 3-[(3-cyanophenyl)methoxy]-5-methylphenyl ester (414 mg, 1.0 mmol), as prepared in step (a) of Example 6, in methylene chloride (10 mL) was added 37% HCl in ethanol (15 mL) at 0° C. The mixture was allowed to stand at 0° C. for 3 days. The solvent was evaporated and the residue was concentrated in vacuo from methylene chloride several times. The residue was dissolved in ethanol (10 mL), treated with methylamine hydrochloride (270 mg, 4.0 mmol) and $Na_2CO_3$ (212 mg, 2.0 mmol), and then stirred at room temperature for 2 days. The reaction mixture was partitioned between methylene chloride (150 mL) and 10% $K_2CO_3$. The organic phase was washed with 10% $K_2CO_3$ (50 mL) and dried over $K_2CO_3$. After removing the solvent in vacuo, HCl in methanol (30 mL) was added and the solvent was removed in vacuo. The residue was then purified by flash column chromatography (10% methanol/methylene chloride) and crystallized from methanol/ethyl acetate to give the title compound as white crystals (145 mg, 30%). $^1$H-NMR (300 MHz, DMSO-d6) δ 2.22 (s, 3 H), 3.01 (s, 3 H), 5.10 (s, 2 H), 6.53 (s, 1 H), 6.56 (s, 1 H), 6.87 (s, 1 H), 7.58 (t, 1 H, J=7.0 Hz), 7.63 (t, 1 H, J=7.6 Hz), 7.73 (m, 2 H), 7.86 (m, 3 H), 7.94 (d, 1 H, J=4.0 Hz), 9.05 (br S, 1 H), 9.55 (br s, 1 H), and 9.94 (br s, 1 H). Mass spectrum (MALDI-TOF, sinapinic acid matrix) calcd. for $C_{22}H_{21}N_2O_4SCl$: 445.1 (M+H). Found: 445.0.

EXAMPLE 16

2-Chlorobenzenesulfonic Acid 3-[(4-Amidinophenyl)methoxy]-5-methylphenyl Ester Hydrochloride a) 2-Chlorobenzenesulfonic Acid 3-[(4-Cyanophenyl)methoxy]-5-methylphenyl Ester Diethyl azodicarboxylate (524 mg, 3.0 mmol) was added to a solution of 2-chlorobenzenesulfonic acid 3-hydroxy-5-methylphenyl ester (900 mg, 3.0 mmol), as prepared in step (c) of the Example 1, 4-cyanobenzyl alcohol (400 mg, 3.0 mmol; Yoon et al., J. Org. Chem. 38:2786–2792 (1973)), and triphenylphosphine (790 mg, 3.0 mmol) in tetrahydrofuran (20 mL) at 0° C. The mixture was stirred at 0° C. for 2 h and at room temperature for 3 h. The reaction mixture was quenched with water (50 mL) and extracted with ethyl acetate (3×50 mL). The organic phase was washed sequentially with saturated $NaHCO_3$ (2×50 mL) and brine (2×50 mL), and dried over $Na_2SO_4$. The solvent was removed in vacuo and the residue was purified by flash column chromatography (2:1 ethyl acetate:hexane) to give the title compound as a white solid (0.95 g, 76%). $^1$H-NMR (300 MHz, $CDCl_3$) δ 2.26 (s, 3 H), 5.03 (s, 2 H), 6.57 (t, 1 H, J=2.2 Hz), 6.59 (s, 1 H), 6.67 (s, 1 H), 7.38 (t, 1 H, J=5.8 Hz), 7.49 (d, 2 H, J=4.2 Hz), 7.60 (m, 2 H), 7.67 (d, 2 H, J=3.5 Hz) and 7.96 (d, 1 H, J=3.6 Hz).

b) 2-Chlorobenzenesulfonic Acid 3-[(4-Amidinophenyl)methoxy]-5-methylphenyl Ester Hydrochloride To a solution of 2-chlorobenzenesulfonic acid 3-[(4-cyanophenyl)methoxy]-5-methylphenyl ester (414 mg, 1.0 mmol), as prepared in the preceding step, in methylene chloride (10 mL) was added 37% HCl in ethanol (20 mL) at 0° C. The mixture was stirred at room temperature for 2 days. The solvent was evaporated and the residue was co-evaporated with methylene chloride several times. The residue was then dissolved in ethanol (20 mL) and ammonium carbonate (385 mg, 4.0 mmol) was added at 0° C. The mixture was stirred at room temperature overnight. The reaction mixture was partitioned between methylene chloride and 10% $K_2CO_3$ (50 mL). The organic phase was washed with 50 mL of 10% $K_2CO_3$ and dried over $K_2CO_3$. The solvent was removed in vacuo. The residue was diluted with $CH_2Cl_2$, treated with HCl in methanol (30 mL), and concentrated. The residue was then purified by crystallization (methanol and ethyl acetate) to give the title compound as a white solid (345 mg, 74%). $^1$H-NMR (300 MHz, DMSO-d$_6$) δ 2.21 (s, 3 H), 5.16 (s, 2 H), 6.53 (t, 2 H, J=9.3 Hz)), 6.86 (s, 1 H), 7.55–7.62 (m, 3 H), 7.82–7.89 (m, 4 H), 7.93 (d, 1 H, J=4.0 Hz), 9.24 (br s, 2 H) and 9.44 (br s, 2 H). Mass spectrum (MALDI-TOF, sinapinic acid matrix) calcd. for $C_{21}H_{19}N_2ClO_4S$: 431.1 (M+H). Found: 431.1.

EXAMPLE 17

2-Chlorobenzenesulfonic Acid 3-[(3-Amidinophenyl)methoxy]phenyl Ester Hydrochloride a) 3-Benzyloxyphenyl Acetate Resorcinol monoacetate (6.10 g, 40 mmol) in DMF (10 mL) was added dropwise to the mixture of NaH (95%, 0.92 g, 40 mmol) in DMF (50 mL). The mixture was stirred at room temperature for 10 min. Benzyl bromide (6.85 g, 40 mmol) in DMF (10 mL) was then added dropwise, and the mixture was stirred at room temperature for 2 h. The reaction mixture was quenched slowly with water (100 mL) and then extracted with ethyl acetate (3×100 mL). The organic phase was washed with brine (2×50 mL) and dried over Na$_2$SO$_4$. The solvent was removed in vacuo and the residue purified by flash column chromatography (1:1 hexane:methylene chloride) to give the title compound as a white solid (5.30 g, 55%). $^1$H-NMR (300 MHz, CDCl$_3$) δ 2.28 (s, 3 H), 5.03 (s, 2 H), 6.72 (m, 2 H), 6.85 (dd, 1 H, J=1.2, 4.1 Hz), 7.27 (t, 1 H, J=7.9 Hz), and 7.41 (m, 5 H).

b) 3-Benzyloxyphenol

3-Benzyloxyphenyl acetate (4.84 g, 20 mmol), as prepared in the preceding step, in tetrahydrofuran (50 mL) was treated with 1 N NaOH (30 mL) at room temperature for 3 h. The mixture was acidified with 1 N HCl and extracted with ethyl acetate (3×100 mL). The organic phase was washed with brine (2×50 mL) and dried over Na$_2$SO$_4$. The solvent was removed in vacuo and the residue purified by flash column chromatography (methylene chloride) to give the title compound as a colorless liquid (3.80 g, 96%). $^1$H-NMR (300 MHz, CDCl$_3$) δ 5.01 (s, 2 H), 5.09 (s, 1 H), 6.47 (t, 2 H, J=2.2 Hz), 6.56 (dd, 1 H, J=1.1, 4.1 Hz), 7.11 (t, 1 H), and 7.39 (m, 5 H).

c) 2-Chlorobenzenesulfonic Acid 3-Benzyloxyphenyl Ester

3-Benzyloxyphenol (2.97 g, 15 mmol), as prepared in the preceding step, in methylene chloride (50 mL) was treated with diisopropylethylamine (2 mL) and 2-chlorobenzenesulfonyl chloride (3.27 g, 15.5 mmol) at 0° C. for 2 h and at room temperature for 2 h. The reaction mixture was diluted with 200 mL of methylene chloride, washed sequentially with saturated NaHCO$_3$ (2×50 mL) and brine (2×50 mL), and dried over Na$_2$SO$_4$. The solvent was removed in vacuo and the residue was purified by flash column chromatography (1:1 hexane:methylene chloride) to give the title compound as a colorless liquid (5.35 g, 95%). $^1$H-NMR (300 MHz, CDCl$_3$) δ 4.97 (s, 2 H), 6.71 (dd, 1 H, J=1.1, 4.1 Hz), 6.78 (t, 1 H, J=2.3 Hz), 6.85 (dd, 1 H, J=1.1, 4.1 Hz), 7.17 (t, 1 H, J=8.3 Hz), 7.37 (m, 5 H), 7.58 (m, 2 H), and 7.91 (dd, 1 H, J=1.1, 4.1 Hz).

d) 2-Chlorobenzenesulfonic Acid 3-Hydroxyphenyl Ester

2-Chlorobenzenesulfonic acid 3-benzyloxyphenyl ester (3.75 g, 10 mmol), as prepared in the preceding step, Pd/C (10%) (350 mg) in tetrahydrofuran (80 mL) was hydrogenated (balloon) for 3 h. The catalyst was filtered through Celite and washed with tetrahydrofuran. The combined tetrahydrofuran solution was evaporated in vacuo and the residue was then purified by flash column chromatography (methylene chloride) to give the title compound as a colorless oil (2.75 g, 95%). $^1$H-NMR (300 MHz, CDCl$_3$) δ 6.68 (m, 3 H), 7.12 (t, 1 H, J=6.5 Hz), 7.37 (t, 1 H, J=7.1 Hz), 7.60 (m, 2 H), 7.94 (dd, 1 H, J=0.6, 4.0 Hz).

e) 2-Chlorobenzenesulfonic Acid 3-[(3-Cyanophenyl)methoxy]Phenyl Ester

Diethyl azodicarboxylate (174 mg, 1.0 mmol) was added to a solution of 2-chlorobenzenesulfonic acid 3-hydroxyphenyl ester (285 mg, 1.0 mmol), as prepared in the preceding step, 3-cyanobenzyl alcohol (133 mg, 1.0 mmol)(Yoon et al, *J. Org. Chem.* 38:2786–2792 (1973)), and triphenylphosphine (263 mg, 1.0 mmol) in tetrahydrofuran (10 mL) at 0° C. The mixture was stirred at 0° C. for 2 hours and at room temperature for 3 hours. The reaction mixture was quenched with water (30 mL) and extracted with ethyl acetate (3×30 mL). The organic phase was washed with saturated NaHCO$_3$ (2×30 mL), brine (2×30 mL) and dried over Na$_2$SO$_4$. The solvent was removed in vacuo the residue was purified by flash column chromatography (2:1 ethyl acetate:hexane) to give the title compound as a pale yellow oil (375 mg, 93%). $^1$H-NMR (300 MHz, CDCl$_3$) δ 5.02 (s, 2 H), 6.78 (m, 2 H), 6.85 (dd, 1 H, J=4.2, 1.3 Hz), 7.20 (t, 1 H, J=8.2 Hz), 7.38 (t, 1 H, J=5.8 Hz), 7.51 (t, 1 H, J=7.7 Hz), 7.59–7.68 (m, 5 H) and 7.93 (dd, 1 H, J=4.0, 0.7 Hz).

f) 2-Chlorobenzenesulfonic Acid 3-[(3-Amidinophenyl)methoxy]phenyl ester Hydrochloride To a solution of 2-chlorobenzenesulfonic acid 3-[(3-cyanophenyl)methoxy]phenyl ester (280 mg, 0.7 mmol), as prepared in the preceding step, in methylene chloride (10 mL) was added 37% HCl in ethanol (15 mL) at 0° C. The mixture was stirred at room temperature for 2 days. The solvent was evaporated and the residue was co-evaporated with methylene chloride several times. The residue was then dissolved in ethanol (10 mL) and ammonium carbonate (300 mg, 3.0 mmol) was added at 0° C. The mixture was stirred at room temperature overnight. The reaction mixture was diluted with methylene chloride (150 mL), washed with 10% K$_2$CO$_3$ (2×50 mL), and dried over K$_2$CO$_3$. The solvent was removed in vacuo, HCl in methanol (30 mL) was added, and then concentrated in vacuo. The residue was purified by flash chromatography (10% methanol in methylene chloride) to give the title compound as a white foam (238 mg, 75%). $^1$H-NMR (300 MHz, DMSO-d6) δ 5.15 (s, 2 H), 6.67 (d, 1 H, J=4.0 Hz), 6.81 (s, 1 H), 7.03 (d, 1 H, J=4.0 Hz), 7.32 (t, 1 H, J=8.3 Hz), 7.58 (t, 1 H, J=7.5 Hz), 7.65 (t, 1 H, J=7.7 Hz), 7.75–7.94 (m, 6 H), 9.27 (br s, 2 H), and 9.45 (br s, 2 H). Mass spectrum (MALDI-TOF, sinapinic acid matrix) calcd. for $C_{20}H_{17}N_2ClO_4S$: 417.1 (M+H), 439.0 (M+Na). Found: 417.4,439.1.

EXAMPLE 18

2-Chlorobenzenesulfonic Acid 3-[5-Amidinopentyloxy]-5-methylphenyl Ester Acetic Acid Salt a) 2-Chlorobenzenesulfonic Acid 3-[5-Cyanopentyloxy]-5-methylphenyl Ester Sodium hydride (24 mg, 1 mmol; 100%) was added to solution of 250 mg (0.855 mmol) of 2-chlorobenzenesulfonic acid 3-hydroxy-5-methylphenyl ester, as prepared in step (c) of Example 1, in 2 mL of N,N-dimethylformamide. After 5 min, 130 μL (0.93 mmol) of 6-bromohexanenitrile was added to the reaction mixture. The reaction mixture was stirred for 2 h at ambient temperature, quenched with brine (50 mL), extracted into diethyl ether (50 mL), washed with water (3×10 mL), dried (MgSO$_4$), and concentrated in vacuo. The residue was purified by flash chromatography (methylene chloride/petroleum ether 4:1 to 100:0) to give 250 mg of the title compound as a colorless oil which solidified upon standing. $^1$H-NMR (300 MHz, CDCl$_3$) δ 7.97 (dd, 1 H, J=1.4, 7.8 Hz), 7.56–7.65 (m, 2 H), 7.36–7.41 (m, 1 H), 6.59 (br s, 1 H), 6.53 (br, s 1 H), 6.48 (t, 1 H, J=1.1 Hz), 3.85 (t, 2 H), 2.38 (t, 2 H), 2.24 (s, 3 H), and 1.6–1.8 (m, 6 H). Mass spectrum (MALDI-TOF, α-cyano-4-hydroxycinnamic acid matrix) calcd. for C$_{19}$H$_{20}$NClO$_4$S: 416.1 (M+Na). Found: 416.1.

b) 2-Chlorobenzenesulfonic Acid 3-[5-Amidinopentyloxy]-5-methylphenyl Ester Acetic Acid Salt A solution of 138 mg (0.351 mmol) of 2-chlorobenzenesulfonic acid 3-[5-cyanopentyloxy]-5-methylphenyl ester, as prepared in the preceding step, in 10 mL of 37% HCl ethanol was stirred at ambient temperature overnight. The reaction mixture was concentrated to an oil, diluted with 5 mL of ethanol and treated with 1.0 g of anmmonium carbonate. Atfer stirring at ambient temperature for 30 min, the reaction mixture was quenched with 2 N NaOH, extracted into methylene chloride, dried (K$_2$CO$_3$), and concentrated. The residue was treated with 500 μL of glacial acetic acid and triturated from diethyl ether/methylene chloride to provide 3.9 mg of the title compound. $^1$H-NMR (300 MHz, DMSO-d$_6$) δ 7.79–7.95 (m, 3 H), 7.55–7.60 (t, 1 H), 6.73 (s, 1 H), 6.49 (s, 1 H), 6.38 (s, 1H), 3.85 (t, 2 H), 2.29 (t, 2 H), and 2.20 (s, 3 H). Mass spectrum (MALDI-TOF, α-cyano-4-hydroxycinnamic acid matrix) calcd. for C$_{19}$H$_{23}$N$_2$ClO$_4$S: 411.1 (M+H). Found: 411.3.

EXAMPLE 19

In Vitro Inhibition of Purified Enzymes

Reagents

All buffer salts were obtained from Sigma Chemical Company (St. Louis, Mo.), and were of the highest purity available. The enzyme substrates, N-benzoyl-Phe-Val-Arg-p-nitroanilide (Sigma B7632), N-benzoyl-Ile-Glu-Gly-Arg-p-nitroanilide (Sigma B2291), N-p-tosyl-Gly-Pro-Lys-p-nitroanilide (Sigma T6140), and N-succinyl-Ala-Ala-Pro-Phe-p-nitroanilide (Sigma S7388) were all obtained from Sigma.

Human α-thrombin and human factor Xa were obtained from Enzyme Research Laboratories (South Bend, Ind.). Bovine trypsin was obtained from Sigma.

K$_i$ Determinations

All assays are based on the ability of the test compound to inhibit the enzyme catalyzed hydrolysis of a peptide p-nitroanilide substrate. In a typical K$_i$ determination, substrate is prepared in DMSO, and diluted into an assay buffer consisting of 5 mM HEPES, 200 mM NaCl, pH 7.5. The final concentration for each of the substrates is listed below. In general, substrate concentrations are lower than the experimentally determined value for K$_m$. Test compounds are prepared as a 0.16 mg/mL solution in DMSO. Dilutions are prepared in DMSO yielding 8 final concentrations encompassing a 200-fold concentration range. Enzyme solutions are prepared at the concentrations listed below in assay buffer.

In a typical K$_i$ determination, into each well of a 96 well plate is pipetted 280 uL of substrate solution, 10 μL of inhibitor solution, and the plate allowed to thermally equilibrate at 37° C. in a Molecular Devices plate reader for >10 minutes. Reactions were initiated by the addition of a 20 μL aliquot of enzyme, and the absorbance increase at 405 nm is recorded for 15 minutes. Data corresponding to less than 10% of the total substrate hydrolysis were used in the calculations. The ratio of the velocity (rate of the change in absorbance as a function of time) for a sample containing no inhibitor is divided by the velocity of a sample containing inhibitor, and is plotted as a function of inhibitor concentration. The data are fit to a linear regression, and the value of the slope of the line calculated. The inverse of the slope is the experimentally determined K$_i$ value.

Thrombin

Thrombin activity was assessed as the ability to hydrolyze the substrate Suc-Ala-Ala-Pro-Arg-pNA. Substrate solutions were prepared at a concentration of 20 μM (20 uM<<K$_m$=180 μM) in assay buffer. Final DMSO concentration was 0.3%. Purified human α-thrombin was diluted into assay buffer to a concentration of 450 nM. Final reagent concentrations were: [thrombin]=0.5 nM, [Suc-Ala-Ala-Pro-Arg-pNA]=20 μM.

Factor Xa

Factor Xa activity was assessed as the ability to hydrolyze the substrate Bz-Ile-Glu-Gly-Arg-pNA. Substrate solutions were prepared at a concentration of 51 μM (51 μM<<K$_m$=1.3 mM) in assay buffer. Final DMSO concentration was 0.3%. Purified activated human Factor Xa was diluted into assay buffer to a concentration of 300 nM. Final reagent concentrations were: [FXa]=20 nM, [Bz-Ile-Glu-Gly-Arg-pNA]=51 μM.

Trypsin

Trypsin activity was assessed as the ability to hydrolyze the substrate Bz-Phe-Val-Arg-pNA. Substrate solutions were prepared at a concentration of 14 μM (14 μM<<K$_m$=291 μM) in assay buffer. Final DMSO concentration was 0.3%. Purified bovine trypsin was diluted into assay buffer to a concentration of 150 nM. Final reagent concentrations were: [Trypsin]=10 nM, [Bz-Phe-Val-Arg-pNA]=14 μM.

Chymotrypsin

Chymotrypsin activity was assessed as the ability to hydrolyze the substrate Suc-Ala-Ala-Pro-Phe-pNA. Substrate solutions were prepared at a concentration of 14 μM (14 μM<<K$_m$=6 uM) in assay buffer. Final DMSO concentration was 0.3%. Purified bovine α-chymotrypsin was diluted into assay buffer to a concentration of 45 nM. Final reagent concentrations were: [chymotrypsin]3 nM, [Suc-Ala-Ala-Pro-Phe-pNA]=14 μM.

The results obtained employing synthesized compounds are given in Table 1.

TABLE 1

| Product of Example Number | Enzyme | K$_i$(μM) |
|---|---|---|
| 1 | Thrombin | 1.65 |
| 5 | Thrombin | 4.86 |
| 6 | Factor Xa | 2.72 |
| 7 | Trypsin | 5.23 |
| 8 | Thrombin | 1.72 |
| 14 | Thrombin | 0.57 |
| 18 | Chymotrypsin | 6.29 |

The results indicate that the compounds of the present invention are inhibitors of proteases. Compounds of the present invention inhibit a number of proteases, including factor Xa, thrombin chymotrypsin and trypsin.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having the Formula II:

$$R^1-Z-\text{[aryl ring with }R^4, R^3, R^2\text{]}-Y-(CH_2)_n-W(R^7)-(CH_2)_m-CH(R^8)-C(=NR^6)-N(R^6)(R^6) \quad II$$

or solvates, hydrates or pharmaceutically acceptable salts thereof; wherein:

Z is selected from the group consisting of $-NR^{10}SO_2-$, $-SO_2NR^{10}-$, $-NR^{10}C(R^yR^z)-$, $-C(R^yR^z)NR^{10}-$, $-OSO_2-$, $-SO_2O-$, $-OC(R^yR^z)-$, $-C(R^yR^z)O-$, $-NR^{10}CO-$ and $-CONR^{10}-$;

$R^y$ and $R^z$ are each independently selected from the group consisting of hydrogen. alkyl, cycloalkyl, aryl, aralkyl, hydroxyalkyl, carboxyalkyl, aminoalkyl, monoalkylaminoalkyl, dialkylaminoalkyl and carboxy;

$R^1$ is selected from the group consisting of alkyl, cycloalkyl, alkenyl, alkynyl, aryl, aralkyl and heteroaryl, any of which may be optionally substituted;

$R^2$, $R^3$ and $R^4$ are each independently selected from the group consisting of hydrogen, alkyl, cycloalkyl, alkenyl, alkynyl, aryl, aralkyl, heteroaryl, trifluoromethyl, halogen, hydroxyalkyl, cyano, nitro, carboxamide, $-CO_2R^x$, $-CH_2OR^x$ and $-OR^x$, or where present on adjacent carbon atoms, $R^2$ and $R^3$ may also be taken together to form one of $-CH=CH-CH=CH-$ or $-(CH_2)_q-$, where q is from 2 to 6, and $R^4$ is defined as above;

$R^x$, in each instance, is independently selected from the group consisting of hydrogen, alkyl and cycloalkyl wherein said alkyl or cycloalkyl groups may optionally have one or more unsaturations;

Y is selected from the group consisting of $-O-$, $-NR^{10}-$, $-S-$, $CHR^{10}$ and a covalent bond;

W is N;

$R^6$, in each instance, is independently selected from the group consisting of hydrogen, alkyl, hydroxy, alkoxy, aryloxy aralkoxy, alkoxycarbonyloxy, cyano and $-CO_2R^w$, where $R^w$ is alkyl or cycloalkyl;

$R^7$ and $R^8$ are taken together to form $-(CH_2)_y-$, where y is 2;

$R^{10}$, in each instance, is independently selected from the group consisting of hydrogen, alkyl, aralkyl, aryl, hydroxyalkyl, aminoalkyl, monoalkylamino($C_{2-10}$)alkyl, dialkylamino($C_{2-10}$)alkyl and carboxyalkyl;

n is from zero to 8, with the proviso that when Y is other than $-CHR^{10}-$, then n is from 2 to 8; and m is from 2 to 4.

2. A compound of claim 1, wherein:

Z is selected from the group consisting of $-SO_2O-$, $-SO_2NR^{10}-$, $-C(R^yR^z)O-$ and $-OC(R^yR^z)-$, where $R^y$ and $R^z$ are each hydrogen;

$R^1$ is selected from the group consisting of $C_{6-10}$ aryl, pyridinyl, quinizolinyl, quinolinyl and tetrahydroquinolinyl, any of which is optionally substituted by one or two of hydroxy, nitro, trifluoromethyl, halogen $C_{1-6}$ alkyl, $C_{1-6}$ alkoxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkoxycarbonylamino, $C_{2-6}$ alkoxycarbonyl, carboxy $C_{1-6}$ hydroxyalkyl, $C_{2-6}$ hydroxyalkoxy, $C_{2-10}$ mono(carboxyalkyl)amino, di($C_{2-10}$ carboxyalkyl)amino, $C_{6-14}$ ar($C_{1-6}$)alkoxycarbonyl, $C_{2-6}$ alkynylcarbonyl, $C_{1-6}$ alkylsulfonyl, $C_{2-6}$ alkenylsulfonyl, $C_{2-6}$ alkenylsulfonyl, $C_{1-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, $C_{2-6}$ carboxyalkyl, $C_{2-6}$ carboxyalkylamino, cyano, trifluoromethoxy, or perfluoroethoxy;

$R^2$, $R^3$ and $R^4$ are independently selected from the group consisting of hydrogen, $C_{1-6}$ alkyl, $C_{3-8}$ cycloalkyl, phenyl, benzyl, trifluoromethyl, halogen, hydroxy ($C_{1-8}$)alkyl, cyano, nitro, carboxamide, carboxy, $C_{1-4}$ alkoxycarbonyl, $C_{1-4}$ alkoxymethyl and $C_{1-4}$ alkoxy; or alternatively, $R^2$ and $R^3$, when present on adjacent carbon atoms, may also be taken together to form one of $-CH=CH-CH=CH-$ or $-(CH_2)_q-$, where q is from 2 to 6, and $R^4$ is as defined above;

Y is selected from the group consisting of $-O-$, $-S-$, $-NR^{10}-$ and a covalent bond;

$R^6$, in each instance, is selected from the group consisting of hydrogen, $C_{1-4}$ alkyl, hydroxy, $C_{1-4}$ alkoxy, phenoxy, $C_{1-4}$ alkyloxycarbonyl and cyano; and $R^{10}$, in each instance, is independently selected from the group consisting of hydrogen, $C_{1-6}$ alkyl, benzyl, phenyl, $C_{2-10}$ hydroxyalkyl, $C_{2-10}$ aminoalkyl, $C_{1-4}$ monoalkylamino($C_{2-8}$)alkyl, $C_{1-4}$ dialkylamino($C_{2-8}$) alkyl and $C_{2-10}$ carboxyalkyl.

3. A compound of claim 1, wherein:

Z is selected From the group consisting of $-SO_2O-$, $-SO_2NR^{10}-$, $-CH_2O-$ and $-OCH_2-$;

$R^1$ is selected from the group consisting of phenyl and naphthyl, optionally substituted by one or two of chloro or dimethylamino;

$R^2$ and $R^3$ are each hydrogen or $R^2$ and $R^3$ may also be taken together to form $-CH=CH-CH=CH-$;

$R^4$ is selected from the group consisting of hydrogen methyl, methoxy and trifluoromethyl;

Y is selected from the group consisting of O and $NR^{10}$;

$R^6$, in each instance is selected from the group consisting of hydrogen and hydroxy;

$R^{10}$, in each instance is independently selected from the group consisting of hydrogen, $C_{1-4}$ alkyl, $C_{1-4}$ hydroxyalkyl, $C_{2-4}$ carboxyalkyl, $C_{2-4}$ aminoalkyl, dimethylamino($C_{2-8}$)alkyl, and methylamino($C_{2-8}$) alkyl;

n is from zero to 4; and m is 2 or 3.

4. A compound of claim 1, wherein Y is selected from the group consisting of $-O-$ and $-NR^{10}-$.

5. A compound of claim 1, wherein Z is selected from the group consisting of $-SO_2NR^{10}-$, $-SO_2O-$ and $-CH_2O-$.

6. A compound of claim 1, wherein:

$R^1$ is selected from the group consisting of $C_{1-12}$ alkyl, $C_{4-7}$ cycloalkyl, $C_{2-8}$ alkenyl, $C_{2-8}$ alkynyl and $C_{6-14}$ aryl, any of which is optionally substituted by one or two of hydroxy, nitro, trifluoromethyl, halogen, alkoxy, aminoalkoxy, aminoalkyl, hydroxyalkyl, hydroxyalkoxy, cyano, amino, monoalkylamino, dialkylamino, carboxy, carboxyalkyl, carboxyalkoxy, mono(hydroxyalkyl)amino, di(hydroxyalkyl)amino, mono(carboxyalkyl)amino, di(carboxyalkyl)amino, alkoxycarbonylamino, alkoxycarbonyl, aralkoxycarbonyl, alkenylcarbonyl, alkynylcarbonyl, alkylsulfonyl, alkenylsulfonyl, alkenylsulfonyl, alkylsulfinyl, alkylsulfonamido, amidino, guanidino, alkyliminoamino, formyliminoamino, trifluoromethoxy or perfluoroethoxy, and when $R^1$ is aryl, cycloalkyl, alkenyl, alkynyl or aralkyl, $R^1$ can be substituted by one or two alkyl moieties.

7. A compound of claim 1, wherein:

$R^2$, $R^3$ and $R^4$ are independently selected from the group consisting of hydrogen, $C_{1-4}$ alkyl, $C_{4-7}$cycloalkyl, $C_{6-14}$ aryl, $C_{6-10}$ $r(C_{1-4})$alkyl, trifluoromethyl, halogen, hydroxyalkyl, cyano, nitro, carboxamide, carboxy, alkoxycarbonyl, carboxymethyl, alkoxycarbonylmethyl, and cycloalkyloxycarbonyl.

8. A compound of claim 1, wherein:

$R^2$ and $R^3$ are attached to adjacent carbon atoms on the benzene ring, and together form —CH=CH—CH=CH— or —(CH$_2$)$_q$—, where q is from 2 to 6, thereby forming a fused ring.

9. A compound of claim 1, wherein $R^6$ is selected from the group consisting of hydrogen, hydroxy, $C_{1-6}$ alkyl, $C_{1-6}$ alkoxy, cyano and —CO$_2$R$^w$, where R$^w$, in each instance, is selected from the group consisting of $C_{1-4}$ alkyl and $C_{4-7}$ cycloalkyl.

10. A compound of claim 1, wherein $R^{10}$ is selected from the group consisting of hydrogen $C_{1-6}$ alkyl, $C_{6-10}$ ar($C_{1-6}$) alkyl, $C_{6-10}$ aryl, $C_{2-10}$ hydroxyalkyl, $C_{2-10}$ aminoalkyl $C_{2-7}$ carboxyalkyl, mono($C_{1-4}$ alkyl)amino($C_{2-8}$)alkyl, and di($C_{1-4}$ alkyl)amino($C_{2-8}$)alkyl.

11. A compound of claim 1, wherein n is 1 to 4, and m is 2 or 3.

12. A compound of claim 1, wherein:

$R^1$ is $C_{6-10}$ aryl, optionally substituted by one or two of hydroxy, nitro, trifluoromethyl, halogen, $C_{1-6}$ alkyl, $C_{1-6}$ alkoxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-10}$ mono(carboxyalkyl) amino, di($C_{2-10}$ carboxyalkyl)amino, $C_{6-14}$ ar($C_{1-6}$ alkoxy)carbonyl, $C_{2-6}$ alkynylcarbonyl, $C_{1-6}$ alkylsulfonyl, $C_{2-6}$ alkenylsulfonyl, $C_{2-6}$ alkenylsulfonyl, $C_{1-6}$ akylsulfinyl, $C_{1-6}$ alkylsulfonamido, amidino, guanidino, $C_{1-6}$ alkyliminoamino, formyliminoamino, $C_{2-6}$ carboxyalkoxy, carboxyalkylamino, cyano, trifluoromethoxy, or perfluoroethoxy.

13. A compound of claim 12, wherein:

$R^1$ is selected from the group consisting of phenyl, chlorophenyl, iodophenyl, dichlorophenyl, bromophenyl, trifluoromethylphenyl, di(trifluoromethyl)phenyl, methylphenyl, t-butylphenyl, methoxyphenyl, dimethoxyphenyl, hydroxyphenyl, carboxyphenyl, aminophenyl, methylaminophenyl, n-butylaminophenyl, amidinophenyl, guanidinophenyl, formyliminoaminophenyl, acetimidoylaminophenyl, methoxycarbonylphenyl, ethoxycarbonylphenyl, carboxymethoxyphenyl, naphthyl, hydroxynaphthyl, cyclohexyl, cyclopentyl, and 2-propylbutyl.

14. A compound of claim 1, wherein $R^2$, $R^3$ and $R^4$ are independently selected from the group consisting of hydrogen, methyl, ethyl, chloro, bromo, trifluoromethyl, hydroxymethyl, methoxy, ethoxy, carboxamide, nitro, phenyl, cyclopropyl, hydroxy, isopropyl, methoxycarbonyl, ethoxycarbonyl and benzyl.

15. A compound of claim 1, wherein $R^6$ is selected from the group consisting of hydrogen, methyl, ethyl, propyl, n-butyl, hydroxy, methoxy, ethoxy, cyano, —CO$_2$CH$_3$, —CO$_2$CH$_2$CH$_3$ and —CO$_2$CH$_2$CH$_2$CH$_3$.

16. A compound of claim 15, wherein each $R^6$ is hydrogen.

17. A compound of claim 1, wherein $R^{10}$ is selected from the group consisting of methyl, ethyl, propyl, n-butyl, benzyl, phenylethyl, 2-hydroxyethyl, 3-hydroxypropyl, 4-hydroxybutyl, 2-aminoethyl, 2-carboxymethyl, 3-carboxyethyl, 4-carboxypropyl and 2-(dimethylamino) ethyl.

18. A compound of claim 1, wherein Y is —O—.

19. A compound of claim 1, having the Formula VII:

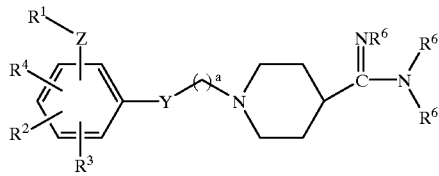

VII wherein:

Z, $R^1$, $R^2$, $R^3$, $R^4$, Y, and $R^6$ are as defined in claim 1, and a is 1 to 8.

20. A pharmaceutical composition for inhibiting proteolysis in a mammal, comprising an amount of a compound of claim 20 effective to inhibit proteolysis.

21. The pharmaceutical composition of claim 20 further comprising a pharmaceutically acceptable carrier or diluent.

22. The pharmaceutical composition of claim 20, comprising an amount of a compound of claim 20 effective to inhibit a trypsin-like protease.

23. A method of inhibiting proteolysis in a mammal, comprising administering to the mammal a composition of claim 20.

24. The method of claim 23, wherein a trypsin-like protease is inhibited.

25. A method of treating pancreatitis, thrombosis, ischemia, stroke, restenosis, emphysema or inflammation in a mammal, comprising administering to the mammal a composition of claim 20.

26. A method of inhibiting thrombin-induced platelet aggregation and clotting of fibrinogen in plasma, comprising administering to the mammal a composition of claim 20.

* * * * *

UNITED STATES PATENT AND TRADEMARK OFFICE
CERTIFICATE OF CORRECTION

PATENT NO. : 6,225,302 B1
DATED : May 1, 2001
INVENTOR(S) : Lu et al.

It is certified that error appears in the above-identified patent and that said Letters Patent is hereby corrected as shown below:

Column 47,
Line 20, delete "hydrogen." and insert -- hydrogen, --.
Line 31, delete "where" and insert -- when --.

Column 48,
Line 1, delete "carboxy" and insert -- carboxy, --.
Lines 5-6, delete "$C_{2-6}$ alkenylsulfonyl" and insert -- $C_{2-6}$ alkynylsulfonyl --.
Line 32, delete "From" and insert -- from --.
Line 33, delete "—$SO_2NR^{10}$," and insert -- —$SO_2NR^{10}$—, --.
Line 39, delete "hydrogen" and insert -- hydrogen, --.
Line 44, delete "instance" and insert -- instance, --.
Lines 45-46, delete "$C_{1-4}$ hydroxyalkyl" and insert -- $C_{2-4}$ hydroxyalkyl --.

Column 49,
Line 2, delete "alkenylsulfonyl" and insert -- alkynylsulfonyl --.
Line 11, delete "$C_{6-10}$r$(C_{1-4})$alkyl" and insert -- $C_{6-10}$ar$(C_{1-4})$alkyl --.
Line 27, delete "$C_{2-10}$ aminoalkyl" and insert -- $C_{2-10}$ aminoalkyl, --.
Lines 42-43, delete "$C_{2-6}$ alkenylsulfonyl" and insert -- $C_{2-6}$ alkynylsulfonyl --.
Line 43, delete "$C_{1-6}$ akylsulfinyl" and insert -- $C_{1-6}$ alkylsulfinyl --.

Column 50,
Lines 38 and 42, delete "20" and insert -- 1 --.

Signed and Sealed this

Sixth Day of June, 2006

JON W. DUDAS
*Director of the United States Patent and Trademark Office*